(12) United States Patent
Donnangelo et al.

(10) Patent No.: US 9,341,687 B2
(45) Date of Patent: May 17, 2016

(54) CLASSIFYING AND IDENTIFYING MATERIALS BASED ON PERMITTIVITY FEATURES

(75) Inventors: Nicholas C. Donnangelo, Purcellville, VA (US); Alexander V. Mamishev, Seattle, WA (US); Walter S. Kuklinski, Princeton, MA (US)

(73) Assignee: The MITRE Corporation, McLean, VA (US)

( * ) Notice: Subject to any disclaimer, the term of this patent is extended or adjusted under 35 U.S.C. 154(b) by 912 days.

(21) Appl. No.: 13/402,538

(22) Filed: Feb. 22, 2012

(65) Prior Publication Data

US 2012/0245873 A1 Sep. 27, 2012

Related U.S. Application Data

(60) Provisional application No. 61/445,190, filed on Feb. 22, 2011.

(51) Int. Cl.
*G01R 33/16* (2006.01)
*G01N 22/00* (2006.01)

(52) U.S. Cl.
CPC ............... *G01R 33/16* (2013.01); *G01N 22/00* (2013.01)

(58) Field of Classification Search
CPC ............................. G01N 22/00; G01R 33/16
USPC ....................................................... 324/639
See application file for complete search history.

(56) References Cited

U.S. PATENT DOCUMENTS

| | | | | |
|---|---|---|---|---|
| 5,914,610 A | * | 6/1999 | Gershenfeld et al. | 324/663 |
| 7,824,619 B1 | * | 11/2010 | Aviram | 422/88 |
| 8,669,771 B2 | * | 3/2014 | Trumper et al. | 324/658 |
| 2003/0085348 A1 | * | 5/2003 | Megerle | 250/287 |
| 2008/0264186 A1 | * | 10/2008 | Nacson et al. | 73/863.12 |
| 2010/0051800 A1 | * | 3/2010 | Atkinson | 250/282 |
| 2012/0175521 A1 | * | 7/2012 | Chawla | 250/339.02 |

* cited by examiner

*Primary Examiner* — Jeff Natalini
(74) *Attorney, Agent, or Firm* — Sterne, Kessler, Goldstein & Fox PLLC

(57) ABSTRACT

Systems and methods are provided for remotely identifying and classifying materials based on their respective complex permittivity features. Materials of interest to be identified in later inspections are cataloged according to their respective complex permittivity features by applying electromagnetic fields to them and determining their complex permittivity features. That library of features is used to compare field measurements taken during an inspection to determine the presence of a material of interest and to identify it.

38 Claims, 33 Drawing Sheets

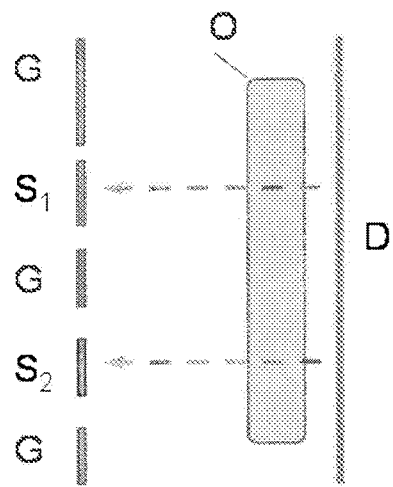
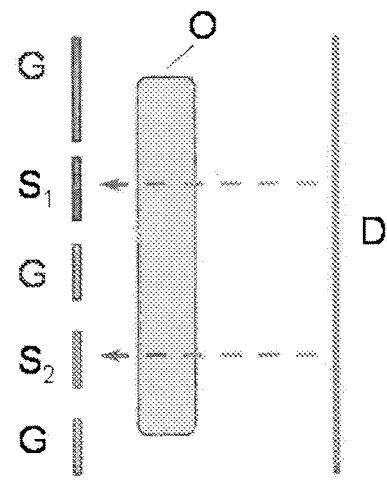
Figure 6a	Figure 6b
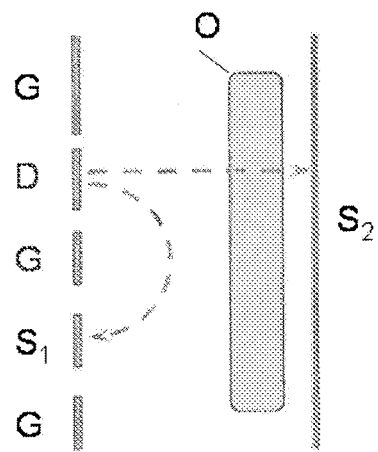
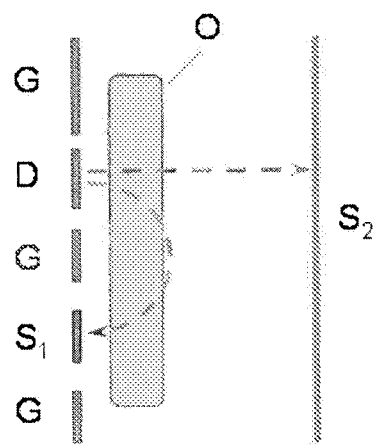
Figure 6c	Figure 6d

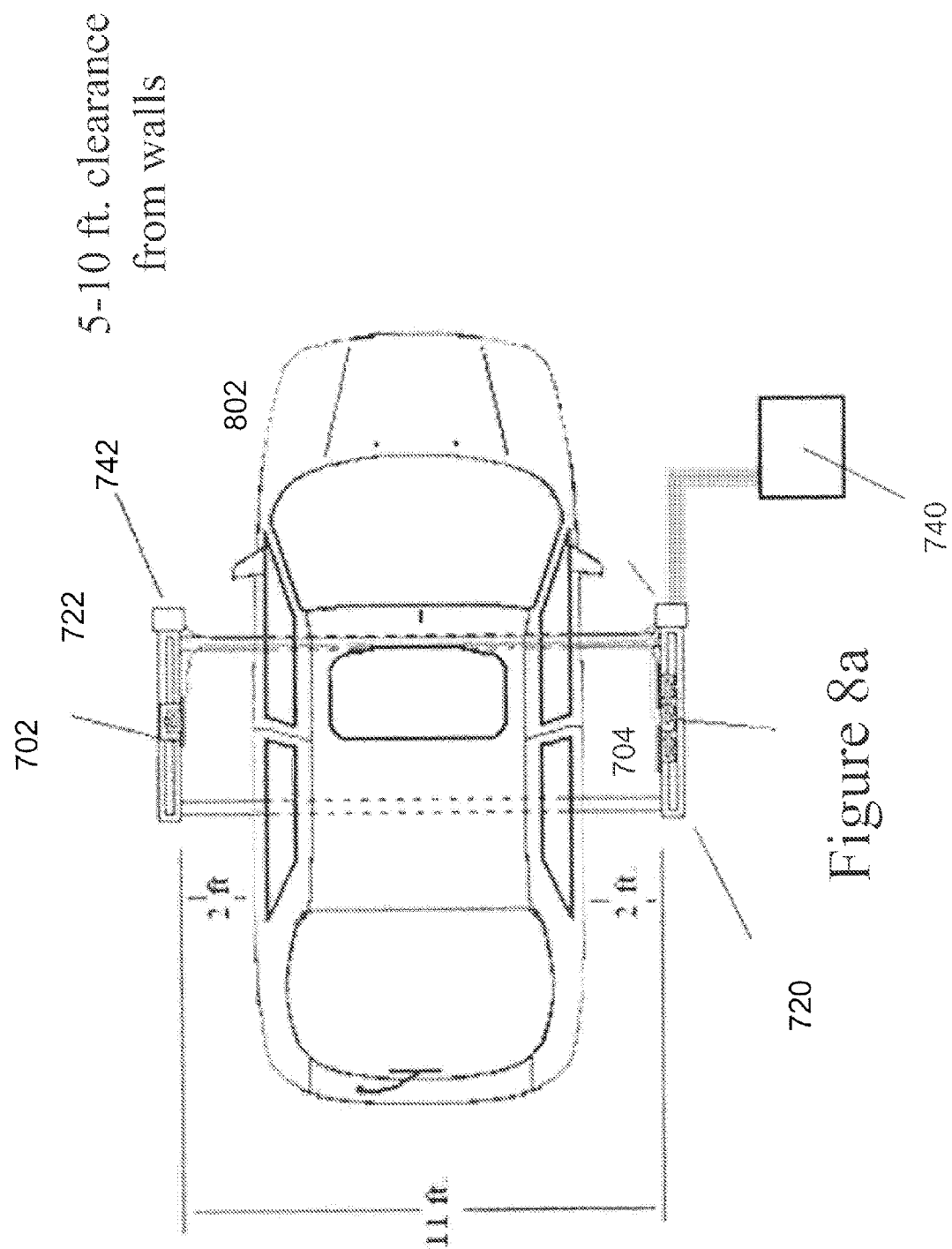

CLASSIFYING AND IDENTIFYING MATERIALS BASED ON PERMITTIVITY FEATURES

CROSS-REFERENCE TO RELATED APPLICATIONS

This application claims the benefit of the filing date of U.S. Provisional Application 61/445,190 filed on Feb. 22, 2011. The subject matter of this application is generally related to that of U.S. patent application Ser. No. 12/395,250 entitled REMOTELY CLASSIFYING MATERIALS BASED ON COMPLEX PERMITTIVITY FEATURES filed Feb. 27, 2009 which is hereby incorporated by reference as if fully set forth herein.

STATEMENT REGARDING FEDERALLY-SPONSORED RESEARCH AND DEVELOPMENT

This is a Statement in accordance with MPEP 310. The U.S. government has a paid-up license in this invention and the right in limited circumstances to require the patent owner to license others on reasonable terms. Part of the work performed during development of this invention utilized U.S. Government funds. The U.S. Government has certain rights in this invention.

BACKGROUND

1. Field of Invention

Embodiments generally relate to remote (non-physical contact) detection and identification of materials, including for example, concealed contraband materials such as explosives, explosives precursors, and narcotics.

2. Related Art

Detection of concealed materials remains very important for military operations, border security, and travel security, especially by air. Although many detection and identification arrangements and methods have been deployed, proposed and attempted, existing detection capabilities remain inadequate.

Detection methods in use at the time of filing this patent document employ various technologies and techniques, including magnetic field sensors, x-ray detectors, radars, terahertz (THz) imaging, odor sensors, and ultrasonic arrays. While detection of even small quantities of metal is relatively easy to do with current technology, such as, for example, magnetic field sensors, detection and discrimination of non-conducting materials is more difficult.

The presence of certain substances can be detected using odor sensors, also known as electronic noses or sniffers. Small numbers of molecules in the air can be detected. However, this approach is inadequate to detect concealed substances. Materials can be either tightly packed, not have sufficient volatility, or be omnipresent in a region where measurements must be made. For example, in a war zone, traces of explosives are commonly present in the air, so detection of explosives is "masked" by ambient levels.

X-ray measurement systems are excellent at providing images of shapes of materials, but have limited capability to distinguish one material from another based on X-ray absorption and/or transmission properties. Many materials of vastly different composition have identical X-ray absorption and/or transmission properties. For example, x-ray images of a book and a rectangular piece of plastic explosive can appear very similar.

In order to better detect and discriminate among materials, what is needed is the ability to determine both a concealed object's shape and provide information about its chemical composition.

BRIEF DESCRIPTION OF THE DRAWINGS

The accompanying drawings, which are incorporated in and constitute part of the specification, illustrate embodiments of the invention and, together with the general description given above and the detailed descriptions of embodiments given below, serve to explain the invention. In the drawings:

FIGS. 6a, 6b, 6c, and 6d depict electrode arrangements and electrode switching schemes and illustrate electric field lines generated by these arrangements.

FIGS. 8a and 8b are top views of vehicle inspection arrangements according to one embodiment of the invention.

Figure 1:
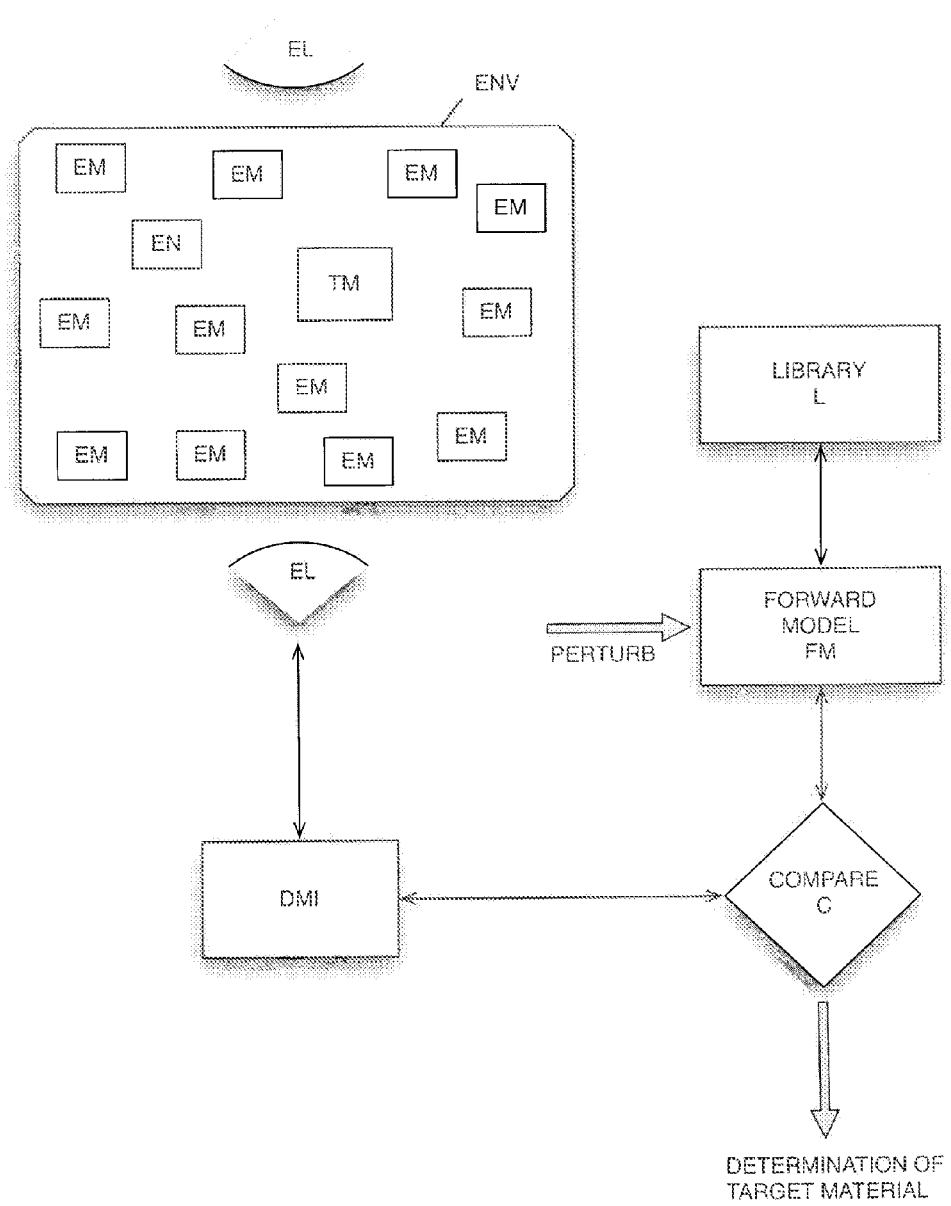
FIG. 1 is a schematic diagram explaining operation of an embodiment of the invention.

Features and advantages of the invention will become more apparent from the detailed description of various embodiments of the invention set forth below when taken in conjunction with the drawings, in which like reference characters refer to corresponding elements throughout. Like reference numbers generally indicate identical, functionally similar, and/or structurally similar elements. In most cases, the drawing in which an element first appears is indicated by the leftmost digit(s) in the corresponding reference number.

DETAILED DESCRIPTION

Introduction

The invention will be better understood from the following descriptions of various embodiments of the invention. Embodiments are physical implementations of the invention (methods and apparatus). Apparatus embodiments are systems and structures made and operated in accordance with the principles of the invention. Method (process) embodiments are methods carried out in accordance with the principles of the invention. Each embodiment provides insight to the invention but may not itself describe the whole invention. In some cases, individual elements of one embodiment may be substituted for similar or corresponding elements of another embodiment carrying out a similar or corresponding function.

The invention relates to apparatus and methods that remotely (i.e., without physical contact) identify target materials based on their respective dielectric properties. Such materials include, but are not limited to explosives, explosive precursors, narcotic drugs, precursors of narcotic drugs, inks used in production of currency, chemical and biological agents. The methods include but are not limited to detecting the presence of these materials, both in isolation and within containers and determining their locations relative to measurement system excitation and sensing electrodes, based on measurements of the complex dielectric permittivity of detected materials. The containers themselves can be made from a combination of dielectric and metal materials. Complex permittivity of a region of an environment containing a target material is determined by probing the region using one or more electromagnetic fields applied steadily or intermittently. These fields may vary in one or more parameters that characterize the fields. For example, the frequency of a field may vary over a wide range of frequencies. Excitation signals are applied to electrodes configured and arranged to induce electromagnetic fields in a region to be inspected. These excitation signals may vary in temporal signal shape and in other characteristics. For example, the excitation signals may have sinusoidal, burst patterns, various wave-shape envelopes, etc. By measuring electromagnetic field changes resulting from the material, the material and its quantity can be determined. At least some of the signal and data processing methods, related hardware and various applications of techniques described in this patent document may be generally referred to as "dielectrometry."

In U.S. patent application Ser. No. 12/395,250 entitled REMOTELY CLASSIFYING MATERIALS BASED ON COMPLEX PERMITTIVITY FEATURES filed Feb. 27, 2009 it was described how materials can be classified and identified based on permittivity. The subject matter of that application is hereby incorporated by reference as if fully set forth herein. Various techniques described herein build upon the teachings of that document and represent improvements based on the methods and apparatus described therein. The amount of information about properties of an unknown material that can be extracted using dielectrometry measurements is limited by the number of independent equations and boundary conditions that can be solved using data obtained from inter-digital sensors and associated instrumentation.

Among various embodiments there will be described a method for remotely determining the presence, quantity, spatial distribution and composition of one or more target materials that may be present in an environment of one or more environment materials, the method comprising:

generating, using at least one pair of electrodes, a first electromagnetic field having a first set of characteristics, the first electromagnetic field being established in a manner such that it interacts with the environment materials and the target material(s) if present;

measuring a trans-impedance between a pair of electrodes to obtain a first trans-impedance;

generating, using at least one pair of electrodes, a second electromagnetic field having at least one characteristic that is changed with respect to the first electromagnetic field, thereby generating a second electromagnetic field having a second set of characteristics, the second electromagnetic field being established in a manner such that it interacts with the environment materials and the target material(s) if present;

then, measuring a trans-impedance between a pair of electrodes to obtain a second trans-impedance;

using a forward model based on a lumped electrical circuit representation of the environment to relate dielectric properties of one or more spatial regions of the environment, to intrinsic dielectric properties of materials and combinations of materials, including the target material(s) as a function of the characteristics of a field; and matching dielectric properties with a library of known intrinsic dielectric properties of a plurality of materials to determine the presence of a target material and its spatial distribution within the environment.

There is also described a method for remotely determining the presence, quantity and spatial location of a target material in an environment including one or more environment materials, comprising:

generating two or more electromagnetic fields having first and second sets, respectively, of characteristics in a manner such that they interact with a combination of materials which may include the material of interest;

first, measuring an impedance between sensor array electrodes to obtain a first set of measurement data;

controlling one or both of the electromagnetic fields so as to change at least one set of characteristics, thereby generating an electromagnetic field having a third set of characteristics;

then, measuring impedances between the sensor array electrodes to obtain a second set of measurement data;

forming, based on measurements taken, a feature tensor quantity including the complex trans-impedances at each of $N(N-1)$ drive and sense electrode pairs over the range of electromagnetic field characteristics such as excitation frequency;

comparing the feature tensor with an equivalent hypothesis tensor including feature vectors derived from controlled measurements, electromagnetic simulations or both by computing the sum of the magnitude of the difference between the complex measurement tensor and the complex hypothesis tensor, which encodes the effect of the object under test on the observability of the material(s) interior, as well as it presence, location and quantity of materials, including material of interest in the spatial region excited by a particular pair of electrodes, a distance metric being computed for each combination of sense and drive electrodes and characteristic of the interacting electromagnetic field such as frequency, the minimum distance corresponding to the compositions and quantity of materials in any location.

There is also described a method for identifying an unknown substance, comprising: first measuring frequency dependent magnetic permeability of the substance; second measuring frequency dependent dielectric permittivity of the substance; and comparing results of the first and second measuring steps with magnetic permeability and dielectric permittivity measurements taken with respect to known materials.

FIG. 1 is a schematic diagram explaining a basic principle and operation of an embodiment of the invention. Using the invention, it is possible to remotely determine the presence, quantity, spatial distribution and composition of one or more target materials TM that may be present in an environment ENV of one or more environment materials EM. A first electromagnetic field having a first set of characteristics is generated using at least one pair of electrodes EL. The first electromagnetic field is established in a manner such that it interacts with the environment materials EM and the target material(s) TM if present. A trans-impedance is measured between the pair of electrodes EL to obtain a first trans-impedance measurement. A second electromagnetic field is generated using at least one pair of electrodes EL, the second electromagnetic field having at least one characteristic that is changed with respect to the first electromagnetic field, the second electromagnetic field having a second set of characteristics and being established in a manner such that it interacts with the environment materials EM and the target material(s) TM if present. A second trans-impedance is measured between a pair of electrodes EL to obtain a second trans-impedance measurement. The electrodes are driven by and trans-impedance measurements are measured by drive and measurement instrumentation DMI. A forward model FM based on a lumped electrical circuit representation of the environment ENV is used to relate, by a comparison process represented by comparator C in FIG. 1, dielectric properties of one or more spatial regions of the environment ENV, to intrinsic dielectric properties of materials and combinations of materials, including the target material(s) TM as a function of the characteristics of a field. The forward model FM can be configured to represent a 2-dimensional environment ENV or a 3-dimensional environment ENV. The forward model FM is perturbed according to various programs until trans-impedance measurements representing dielectric properties are reasonably matched to dielectric properties represented by information in a library L of information representing known intrinsic dielectric properties of a plurality of materials to determine the presence of a target material TM and its spatial distribution within the environment ENV.

Frequency Dependence

It is now recognized that it can be advantageous to utilize an AC interrogating electromagnetic field that is as broadband as practical to exploit frequency dependent changes in the complex dielectric permittivity of an environment containing an unknown material. The frequency and other characteristics of an interrogating field probing an unknown material can be varied to distinguish between materials having otherwise similar "signatures" but exhibit characteristic signatures over a wide band. As part of an interrogating process, the frequency of an interrogating field can be varied in various ways. For example, the frequency can be varied in a continuous manner from one frequency to another. The interrogating field can be applied as bursts of signals at the same or different frequencies, and at different voltages. A predetermined interrogation program of changes to an interrogating field can be stored for future use and carried out in an automated fashion. Such a predetermined interrogation program may include changes of frequency, wave shape and other parameters. A program of frequency and other parameter changes can be integrated with signal processing for material classification such that characteristics of the interrogating field can be adaptively changed to resolve classification ambiguities. An interrogation program may control the interrogating field so that it varies according to a complex program of frequency changes, bursts and the like. The frequency spectrum of the interrogating signals can be contiguous or non-contiguous.

The range of frequencies that are useful for interrogating unknown materials is from extremely low frequency (ELF) to near infrared (NIR) frequencies. The frequencies to use in a particular interrogation are selected based on a number of factors including the suspected composition of the material to be identified, and its container composition, physical size of material to be identified, the type of material, location, etc. Frequencies can be selected a priori based on a particular perceived threat or they can be changed in a pre-programmed manner. Based on the invention, particular applications of the invention can be developed for investigating various types of perceived threats. For example, if it is desired to detect a particular substance that has features that become evident in particular regions of the spectrum between ELF to NIR wavelengths, those wavelengths are selected to optimize ability to distinguish that particular substance from other substances.

Figure 2A:
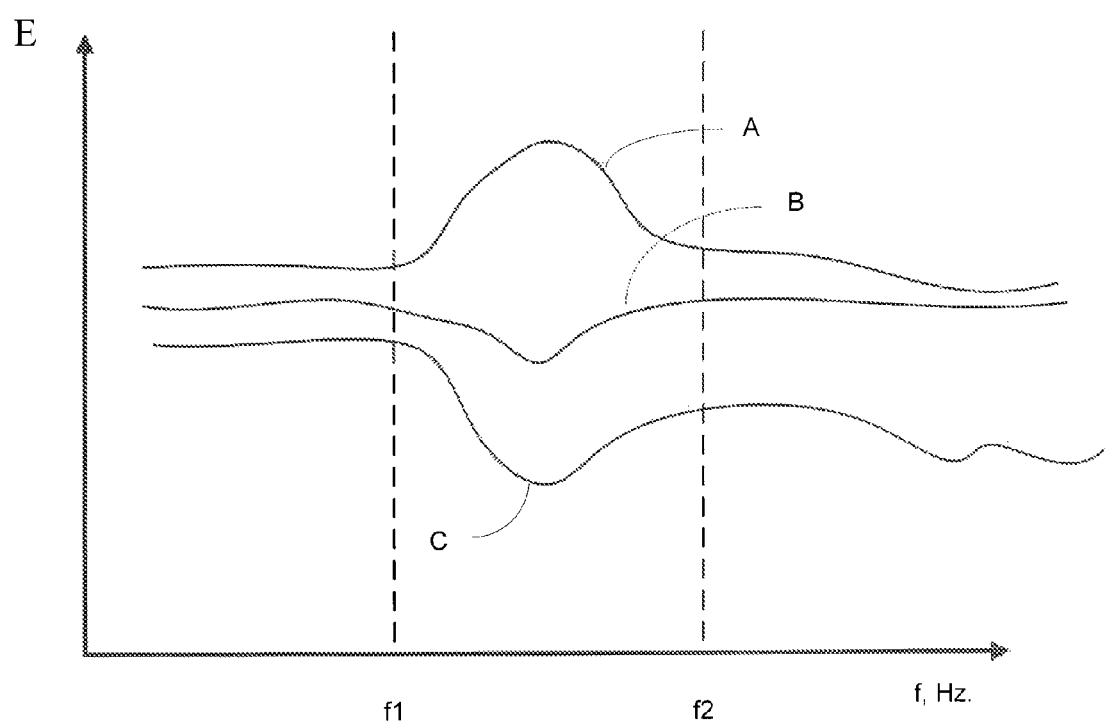
FIG. 2a graphically depicts a hypothetical broadband frequency scan of three materials, A, B, and C demonstrating the principle that they can be differentiated based on electromagnetic field measurements at different frequencies.

FIG. 2a graphically depicts a hypothetical broadband frequency scan of three materials, A, B, and C and helps to illustrate a principle of the invention. Materials A, B and C, are each placed in a region in which an electromagnetic field can be generated by a field generating electrode and changes to the electromagnetic field can be measured by a field sensing electrode. Different materials produce different measurable signals at the field sensing electrode when interrogated over a range of frequencies. Although the figure is quite general, the principle illustrated by the graphical representation can be applied in various ways and manners to determine whether particular materials are present and to distinguish among various materials to accurately identify them. The measurement variable, represented by the horizontal axis, is frequency. The response, represented by the vertical axis, is a signal level (voltage) induced at a sensing electrode by the interrogating field passing through the material and potential container. The response is related to the complex dielectric permittivity of the material being interrogated and a number of environmental variables such as the amount and location of the material within the container (i.e. a vehicle or shipping crate) and the geometrical relationship between the excitation and sensing and electrodes and the container. Materials are characterized by their "complex dielectric permittivity signatures" i.e. a combination of functions that represent the dependence of real and imaginary parts of dielectric permittivity on excitation frequency.

According to an embodiment of the invention, a training process is carried out to develop a library of complex dielectric permittivity signatures of materials. To produce this library, known materials are "interrogated" by producing one or more fields at various frequencies and under various interrogating field conditions with various electrode arrangements. Based on their respective dielectric characteristics, various materials subjected to electric fields cause the fields to change in different ways. By measuring the effects on the fields by the materials, a complex dielectric permittivity signature is determined for each material. These complex dielectric permittivity signatures include responses caused by the material at multiple locations within interrogating fields, responses caused by various quantities of a material, and responses caused by the material when it is in proximity to other materials. For ease of explanation "complex dielectric permittivity" will be referred to as "permittivity." These permittivity signatures are stored, cataloged in a library and used later for comparison with permittivity signatures of unknown materials to aid in their identification.

For example, to identify candidate materials A, B and C, multiple interrogation field scans of an unknown material sample are made using those frequencies that are most likely to distinguish the candidate material from all other materials. Frequencies useful for identifying these materials and distinguishing them from other materials may, for example, be in a range of frequencies between f1 and f2. If it is desired to specifically detect and identify these particular materials, scans can be carried out in the range of f1 to f2, allowing discrimination in a shorter period of time than if a wider range of frequencies were used. Given that measured permittivity signatures are only partially dependent on a given material, i.e., the measured signature is strongly influenced by location in the interrogating field, quantity, nearby objects and characteristics of the surrounding container, when present, scans with specific objectives can be customized in order to quickly detect a candidate material from among others. On the other hand, if one seeks to identify a wide range of materials, additional data collection time is needed to make a broad initial scan (wider range of frequencies) followed by a second and possibly further customized scans, designed to resolve ambiguities that may be present in data from the initial scan.

Figure 2B:
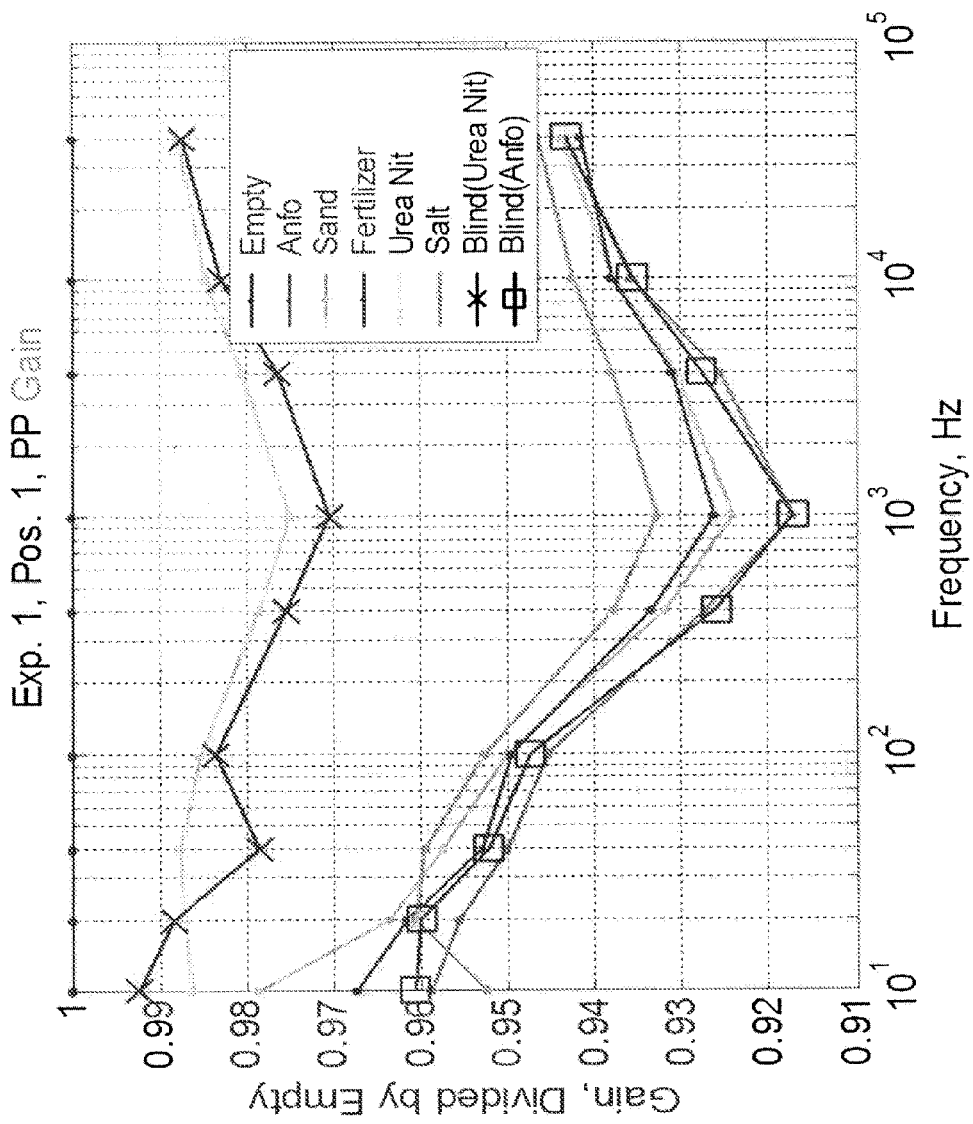
FIGS. 2b, 2c, 2d and 2e graphically depict exemplary signature sets of various materials by displaying measurable aspects of their respective intrinsic dielectric properties, the materials including, for example, sand, fertilizer, and urea.
Figure 2C:
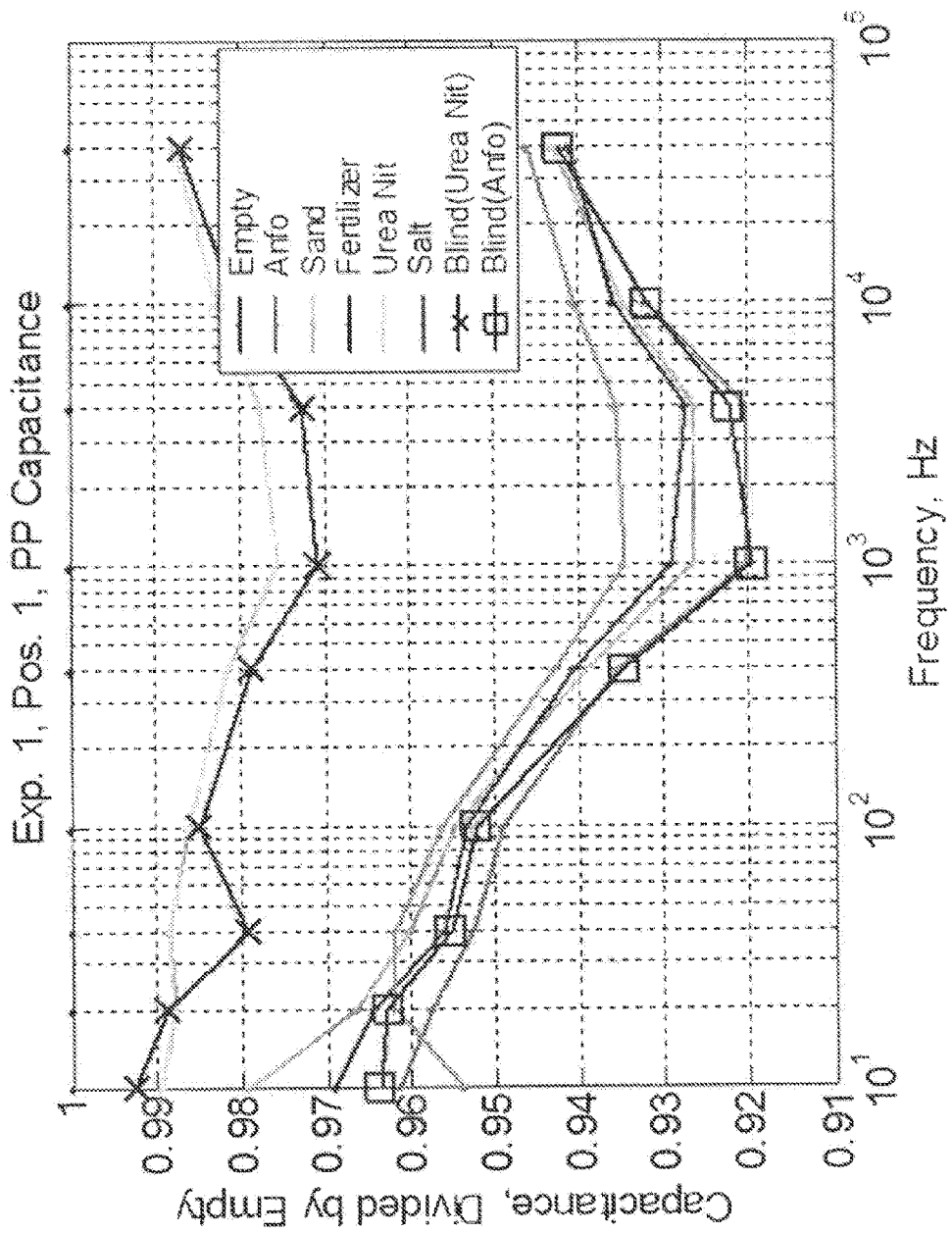
Figure 2D:
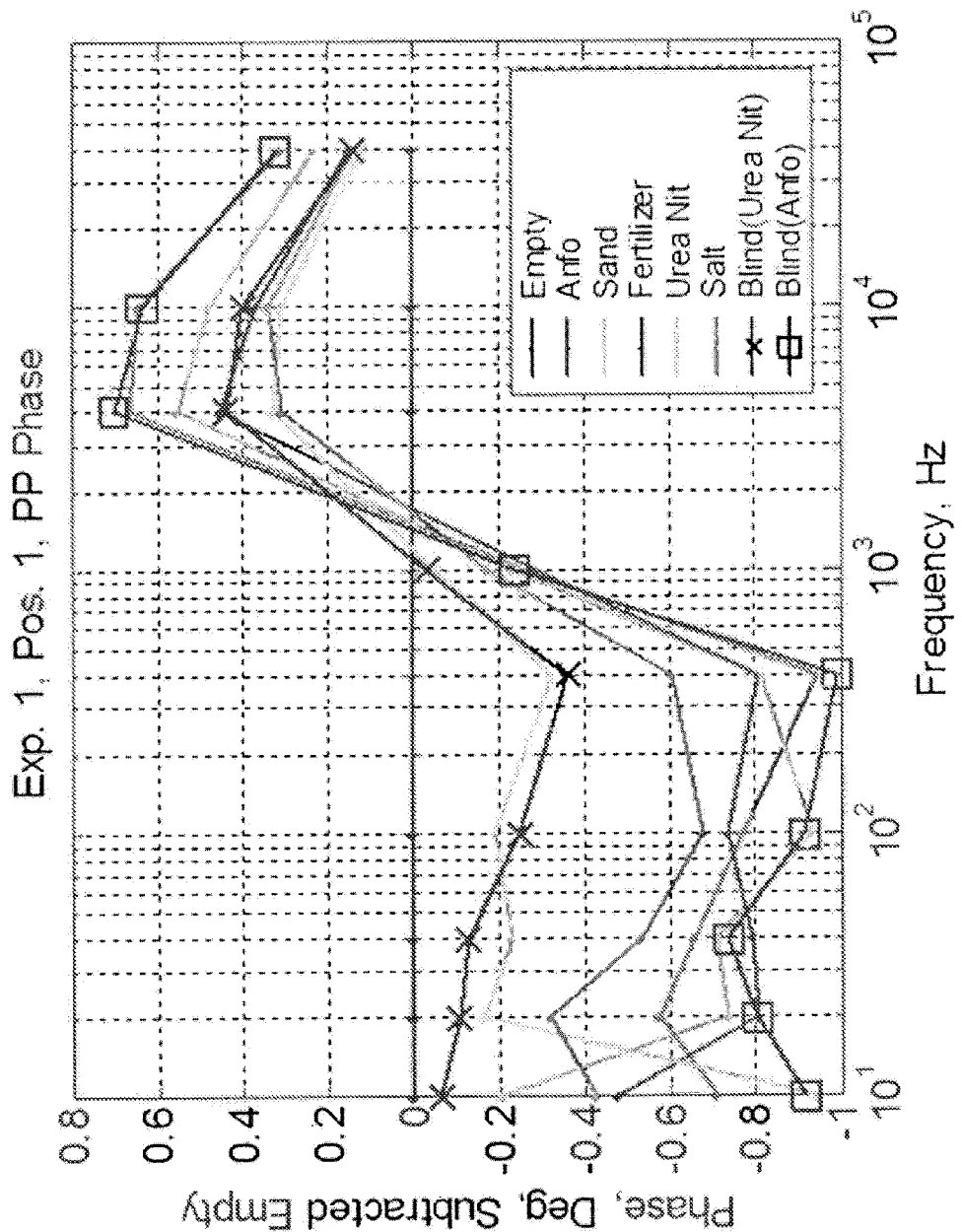
Figure 2E:
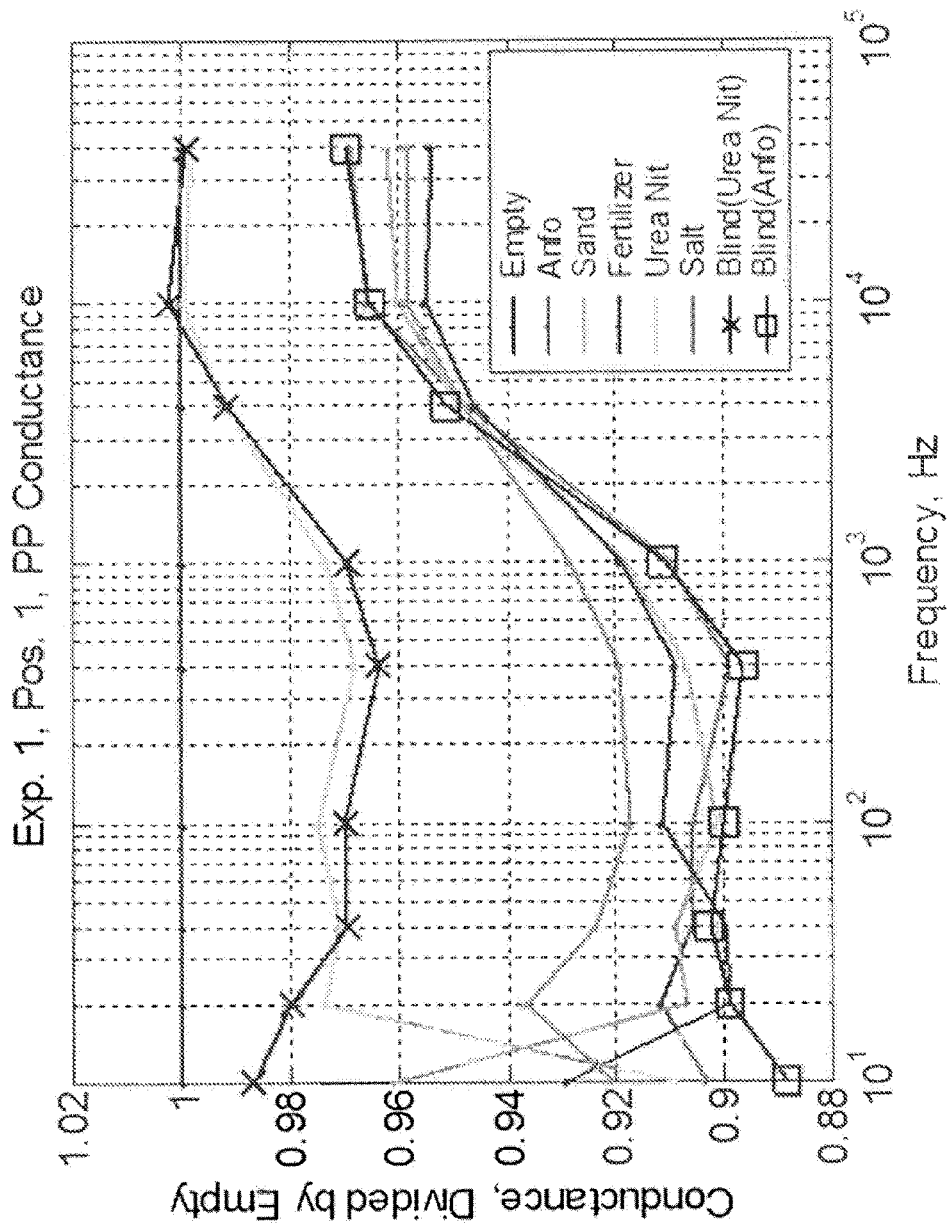

FIGS. 2b, 2c, 2d and 2e graphically depict various aspects of exemplary signature sets for various materials including, for example, sand, fertilizer, urea, etc. The graphical representations plot data from actual measurements of responses to interrogating fields made with predetermined electrode arrangements under predetermined conditions. Generally, the shape of non-differential measurement signatures (i.e., single measurements made where a material of interest is within a container) are highly dependent on the overall geometry of measurement infrastructure including, e.g. distance between the electrodes, size of container (e.g. car), etc; whereas pairs of differential measurement (made both with and without the material of interest being present in a container) can be jointly processed to reveal characteristics associated with materials and less dependent on the overall geometry of measurement infrastructure. For the various materials listed in keys shown in respective figures, FIG. 2b is a graphic representation of gain vs. frequency, FIG. 2c is a graphic representation of capacitance vs. frequency, FIG. 2d is a graphic representation of phase vs. frequency, and FIG. 2c is a graphic representation of conductance vs. frequency. The library of dielectric characteristics of materials developed during training may include a few or many of various measures and indicators of complex dielectric permittivity. These measures and indicators might include, for examples, capacitance, measured trans-impedance between electrodes, etc. Each of the graphic representations of FIGS. 2b, 2c and 2d are normalized with respect to an empty space.

Full Tomography Embodiment

An embodiment of the invention utilizes a "full (pure) tomography" process to determine whether or not a material of interest is present and if so where the material is positioned. In this full tomography process trans-impedance measurements made of an object under inspection are compared with complex permittivity signatures previously cataloged in a library (earlier compiled complex permittivity actual measurements of various materials). A "forward model" (lumped element equivalent circuit in FIG. 26) represents a hypothetical unidentified material as part of a "system" including the unknown material and its surroundings. For example, in the case of an unidentified material in a vehicle, the "system" would include the vehicle, a container holding the unidentified material and the unidentified material itself. The forward model describes a complex response of the "system" to an interrogating electromagnetic field. The use of a forward model allows tomographic inversion techniques to be employed to separate responses due to the unidentified material from responses due to other elements of the system, taking into account overall geometry of the system and measurement infrastructure.

Using the full tomography process, for example, a vehicle that may or may not contain a material of interest is positioned within an array of electrodes. Various electrodes are driven according to a program to establish interrogating fields. Non-driven electrodes sense voltages induced by the interrogating fields as modified by the vehicle and its contents. The result of the program of measurements is a set of measured voltages at the various electrodes. These measured voltages are matched to voltages that would be expected to occur, based on the forward model, for the various materials previously cataloged in a library. The forward model effectively links the information stored in the library (previously developed through extensive experimentation) to present day measurements taken during an inspection. For example, if the vehicle under present inspection contains one pound of material X in its trunk, one would expect to see certain voltages measured at certain electrodes based on the forward model translating (inverting) the matrix of information stored in the library. The forward model is, in effect, a set of simultaneous equations describing the arrangement of lumped elements shown in FIG. 26. That set of equations is repeatedly perturbed in different ways until a good fit is found between measured data from the current inspection and data found in the library. The forward model inverts the data from the library into expected trans-impedance measurements that are readily compared with current measurements being taken during inspection.

The forward model is perturbed until the best fit is found in the library for current inspection measurement data. When a best fit is determined, there is an attempt to determine whether that best fit truly represents an unambiguous match to certain library data. This process tests the "goodness" or "variance" of the best fit decision. One way to carry out that determination is to look not only at the best fit, but also look at the second best fit. If the second best fit is far removed from the best fit, it is considered to be likely that the best fit is not ambiguous. However, if the second best fit is close to the best fit, the best fit is considered to be ambiguous.

Ambiguous best-fit data can be resolved in various ways and manners. For example, to continue in a non-intrusive inspection, electrodes can be repositioned and new measurements made. Again, the results are compared with library data based on the perturbation of the lumped element forward model. A judgment can again be made as to whether a best fit resulting from repositioned electrodes is not ambiguous.

Another exemplary process to continue in a non-intrusive inspection is to energize the electrodes in a different manner, such as using different frequencies, a different program of frequency changes, wave form shapes, etc. Measurement results from the changed program are compared with library data based on the perturbation of the lumped element forward model. A judgment can again be made as to whether a best fit resulting from repositioned electrodes is not ambiguous.

As another example, for a given type of inspection if the response to an initial ambiguous determination may lead to physical inspection being carried out rather than simply relying on an automated inspection based on permittivity features.

Intermediate Tomography Embodiment

Another embodiment of the invention utilizes a simplified measurement technique referred to as "intermediate tomography" to determine whether or not a material of interest is present and if so where. The intermediate tomography process is simpler to utilize and is effective for certain types of inspections. In the intermediate tomography process trans-impedance measurements made of an object under inspection are compared with trans-impedance measurements of similar objects previously made. The previously made measurements may include measurements made during actual previous inspections. The forward model is not used. The library of data to which current inspection measurements are compared is in the same form as measured data being taken "live". Thus, less computation is required and the comparison can be carried out quickly and easily without the need for robust computing power.

For example, using the intermediate tomography process, a vehicle that may or may not contain a material of interest is positioned within an array of electrodes. Various electrodes are driven according to a program to establish interrogating fields. Non-driven electrodes sense voltages induced by the interrogating fields as modified by the vehicle and its contents. The result of the program of measurements is a set of measured voltages at the various electrodes. These measured voltages are matched to voltages previously stored in a library of such measured voltages. In that library, measured voltages correspond to various materials that were found to be present when the library measurements were taken. There is no inversion of cataloged data through a lumped element forward model as in the case of the use of "full tomography".

Using the intermediate tomography process, one can also carry out an analysis to determine of current measured data is a good fit to previously measured data. The same kind of determination is made to determine whether a current "best fit" truly represents an unambiguous match to certain library data. The "goodness" or "variance" of the best fit match can be carried out in the same manner and responses to the determination can be made appropriately to the situation. For example, further measurements may be made with an altered electrode arrangement, a different program of excitation frequencies, wave shapes, etc, can be carried out during further measurements. A physical inspection may be carried out in place of further non-invasive testing.

Adapting Scan (Interrogation)

Figure 3:
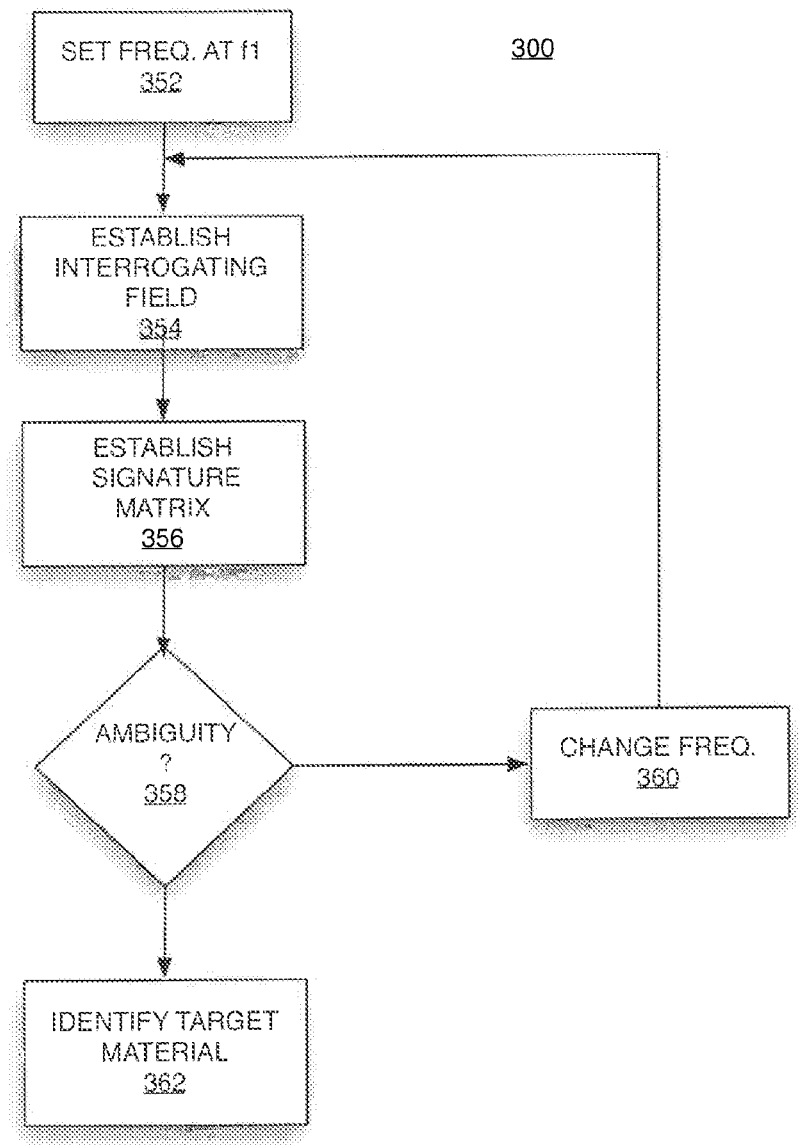
FIG. 3 is a flow chart of a process embodiment of the invention for resolving the identity of an unknown target material by changing frequency of an applied field.

Frequency and frequency band are significant parameters of an interrogating field used to identify the presence of a material and distinguishing it from other materials. FIG. 3 is a flowchart of a generic process 300 of adaptive frequency selection according to an embodiment of the invention. An initial electromagnetic field frequency f1 is established at 352. At 354 an unknown material to be identified is initially scanned using a limited bandwidth interrogating field. A signature matrix library is established at 356. A relatively simple signature matrix includes at least complex impedance (impedance amount and phase of impedance) as a function of frequency. A more complex library may include additional parameters, such as, for example, loss tangent as a function of frequency. Based on results of the initial scan, the unknown material could potentially be identified at 358 to be any of a number of materials that might have similar features based only on the initial scan at 354. Thus, at a particular frequency f1, there may be an ambiguity at 358 in identifying an unknown material. These material classification ambiguities at 358 are resolved by second and subsequent, as needed, scans using programs of frequency, waveform, etc. chosen specifically to resolve the ambiguities by distinguishing among materials having similar properties in the initial scan. For example, material A may look similar to material B at frequency f1, but may look very different from material B at frequency f2 (see FIG. 2a). As another example, six different materials may look similar over a first range of frequencies, but look very different from one another in other ranges of frequencies. The ambiguity in distinguishing between materials is resolved by changing frequency at 360 and again establishing an interrogating field at 354 for rescanning. This process of changing frequency and frequency band continues until there is no further ambiguity and the material is identified at 362.

Embodiments of the invention integrate signature measurements over a number of interrogating "cycles" (sets of measurements) to reduce the effect of noise. Under certain circumstances at lower frequencies, latency may require that the number of measurement cycles be reduced thereby increasing noise during low frequency measurements. In certain cases of ambiguous material classification, lower frequencies become more important to ambiguity resolution and longer scans may be necessary. Longer integration doesn't always provide better quality data at lower frequencies, in some cases long integration can introduce more noise than it provides gain in signal. Integration time can be determined and set to achieve an optimal signal to noise ratio.

Ambiguities can be resolved by increasing a measured feature set. According to an embodiment of the invention, an increased feature set can be used to test a specific classification hypothesis. For example, if it is hypothesized that an unknown material "looks like opium", one can conduct and compare subsequent measurements designed specifically to distinguish opium from other materials. A group of permittivity features distinguishing a particular material is referred to herein as a "template". A material's "template" may include a feature set capable of distinguishing it from other materials.

In addition to selective excitation to resolve ambiguities, another approach is to widen the interrogating wavelength band to include a higher dimensioned classification vector. Higher dimensionality in the feature vector allows for greater discrimination. There is a tradeoff between accurate classification (considering false alarms and false positives) and computation time and classification latency. The dimensionality of a feature vector can be adaptively controlled to strike a desired balance between false alarms and false positives for a particular classification attempt, taking into consideration computation time required.

While parameters such as quantity and location in the interrogating electric fields change the measurement of permittivity, these measurements are still exploited in the invention to allow for detection of materials regardless of their amount or placement within a sensing field.

Differentiation of Materials

Figure 4:
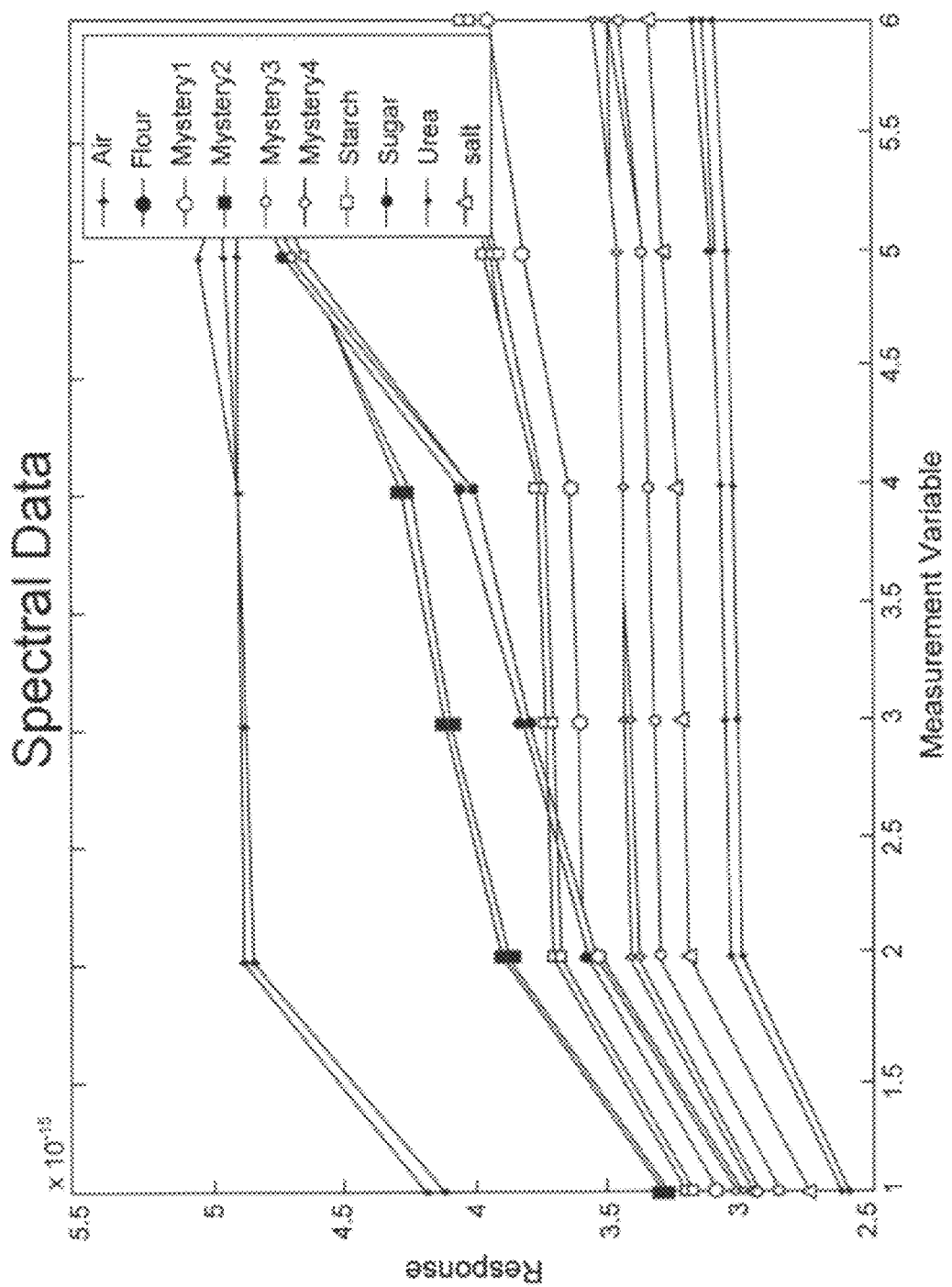
FIG. 4 graphically depicts an example of weight-independent differentiation among several materials.

FIG. 4 graphically depicts an example of weight-independent differentiation of several materials. First, signatures of flour, sugar, salt, urea, and no material (just air) are measured. Then, unknown materials are identified via comparison of signature features. Material marked "Mystery1" follows the permittivity signature (any of several different dielectric parameters in the permittivity matrix) of starch very closely. Signatures of materials marked "Mystery2" and "Mystery3" overlap with each other and are very close to the known signature of sugar. In these examples, the quantities of all materials were kept the same. However, the principle also applies for different quantities of material. The signature of "Material 4" is far from the signature of starch in absolute terms, because the quantity of starch in this experiment is half that of "Mystery1". However, one can still identify this material as starch by considering other permittivity signatures (e.g., lost tangent) and/or considering the first derivative of the signature, identifying inflection points and cusps of the permittivity data. Across the full range of permittivity response, derivative as a function of frequency and the partial derivatives of a particular permittivity response with respect to other permittivity variables, d(capacitance)/d(impedance) ambiguities are resolved in material identification.

In embodiments of the invention, signature identification is based on automated methods using any known classification and pattern recognition algorithms, for example but without limitation, a K-nearest-neighbor algorithm. The following describes a signature collection and analysis process for the simplest forward model contemplated in the invention, a single parallel RC circuit.

Electrode Arrangement and Structure

Figure 5:
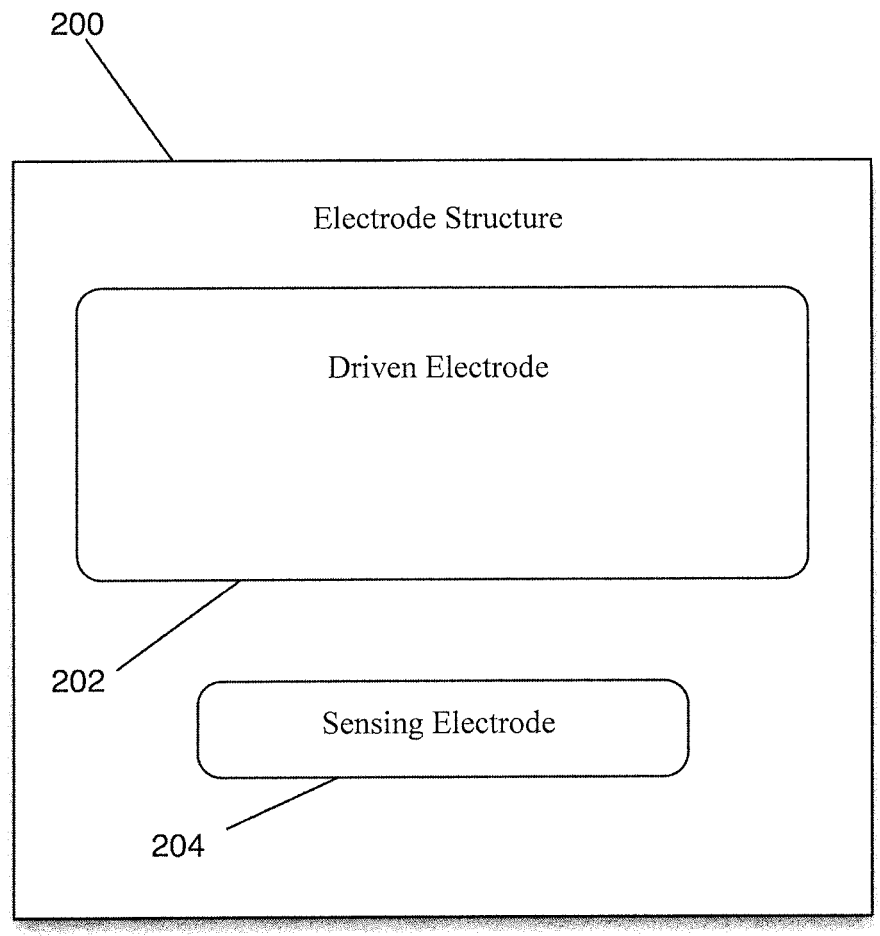
FIG. 5 is a schematic diagram of a configuration of an electrode assembly useful to operate in both drive and sensing modes, the electrode assembly being suitable for use in practicing various embodiments of the inventions.

FIG. 5 is a schematic diagram of one configuration of an electrode structure 200 suitable for use in various embodiments of the invention. Electrode structure 200 includes a driven electrode 202 and a sensing electrode 204. Measurement instrumentation used for dielectric measurements has to be highly sensitive, stable and accurate. Since the equipment is subject to electronic drift, it is advantageous to self-calibrate it frequently, possibly before every measurement. A measurement circuit can be calibrated by switching sensing electrode 204 periodically from a measurement position to a position where the distance between the sensing electrode 204 and driven electrode 202 is very small and only air properties are measured. Thus, the electrodes can be operated in a measuring position and in a calibrating position. One arrangement for calibrating is to form the sensing electrode 204 as a strip in the plane of the driven electrode 202, as illustrated in FIG. 5. Other electrode arrangements are possible.

Electrode arrangements, excitation patterns and corresponding sensing modes (parallel plate vs. fringing field) can be optimized to increase probability of detection and probability of correct classification, to reduce false alarms and further to identify and refine spatial information.

Planar electrodes of various shapes can generate fringing fields into the material under test. Different electrode shapes may be used to increase capacitance, to concentrate the electric field at a specific location, to optimize specific spatial Fourier components of the electric potential in order to change the effective penetration depth, and to exploit symmetry of the material under test.

The actual electrode excitation pattern and corresponding sensing mode (parallel plate vs. fringing field) can be optimized to increase probability of detection and probability of correct classification, to reduce false alarms and further to identify and refine spatial information.

Planar electrodes of various shapes can generate fringing fields into the material under test. Different electrode shapes may be used to increase the capacitance, to concentrate the electric field at a specific location, to optimize specific spatial Fourier components of the electric potential in order to change the effective penetration depth, or to exploit symmetry of the material under test.

An embodiment of the invention provides an electrode arrangement including a shielded co-axial cable having an inner conductor and an outer shell and a spacer insert positioned between the inner conductor and outer shell so as to reduce capacitance therebetween.

Using various electrode arrangements an embodiment of the invention provides a method for measuring dielectric properties wherein drift of measurement instrumentation and associated cabling is used to normalize the measurement data.

An embodiment of the invention provides a dielectric measurement electrode arrangement including a shielded air capacitance cell and means for quantifying in real time a drift of measurement instrumentation and associated cabling based on a capacitance of the shielded air capacitance cell.

FIGS. 6a, 6b, 6c and 6d depict some of the possible electrode arrangements and electrode switching schemes according to embodiments of the invention. They include a schematic indication of electric field lines generated by these arrangements. Previous efforts to categorize and identify unknown materials utilized two different scanning methodologies: a) parallel plate, and b) fringing field, but in a limited sense. According to this invention, it is recognized that it is advantageous to adapt a scan of an unknown material under test by scanning according to both methodologies, i.e. by switching between parallel plate and fringing field measurements, and by switching among various parallel plate and fringing field excitation patterns across a multi-channel architecture. Scanning using both the parallel plate and fringing field arrangements makes it possible to (i) resolve classification ambiguities or unacceptably high uncertainties on a classification decision and (ii) resolve spatial ambiguities or unacceptably high uncertainties of spatial estimation.

Measurement data obtained from a parallel plate electrode arrangement represents a lateral cut through an unknown material under test. Multiple parallel plates can be used to produce data representing different lateral cuts. Measurement data obtained from fringing field electrode arrangements represents cuts in a plane orthogonal to the parallel plate measurement plane. The target is "cut" longitudinally. Fringing field sensing can sense out of plane "depth." For fringing field sensing, penetration along the plane orthogonal to the electrodes is proportional to the spacing between "in plane" electrodes; i.e., the greater the baseline between the electrodes the greater the out of plane penetration and the distance that the longitudinal cut is made. In practice this means that as the electrodes are spaced from the closest to the furthest, successive longitudinal "slices" are made through the item of interest. This closest spacing to widest spacing set of fringing field measurements is repeated on the other side. There is a latency associated with scans so the number of scans and the range of frequencies (particularly on the low end) are minimized. The pattern of which electrode is energized and activated in either mode can be adaptively controlled by a classification algorithm to remove classification ambiguities or spatial uncertainty.

Reduced Order Tomography

FIGS. 6a, 6b, 6c and 6d together schematically illustrate an arrangement and method that can be used to determine position of the object as well its material composition at the same time using the assumption that the material under test and any associated container (including but not limited to box or parcel, shipping container, trailer or car or other vehicle) can be modeled as a single parallel RC circuit. The circuit model could also include inductance. This approach is therefore described as a "reduced-order" tomography approach. Properties of interest are determined without solving a complete inverse problem for a given arrangement of electrodes. This mathematical simplification results from assumed partial knowledge about the properties of some regions of interest. For example, this embodiment exploits an assumption that the volume around the object of interest contains only air and that no other objects are present in the field of measurement.

The electrode arrangement shown in FIGS. 6a, 6b, 6c and 6d include driven electrodes D, sensing electrodes S, and guard electrodes, G. The object of interest (to be detected/measured for the possible presence of contraband material) is denoted as O. Electronic switching is used to assign different roles to the various electrodes.

FIGS. 6a and 6b schematically show a switching arrangement in which electric field lines penetrate through an air gap and a material of interest to be detected and identified. In this arrangement, the impedance between the drive electrode and each of the sensing electrodes does not change even if the object of interested moves horizontally, because the two series air gap capacitances add to the same number for every position of the object. Therefore, this arrangement can be used to determine the material properties without determining its position. The signal is exactly the same in both arrangements, A and B, unless the object moves sufficiently far in the vertical position.

FIGS. 6c and 6d schematically show two different locations of the object of interest under a different switching scheme. In both schemes, the impedance between the driven electrode D and the sensing electrode S2 remains essentially the same even if the object moves in the horizontal direction, because the series capacitance of air gap is the two gaps between the object O and the electrodes S2 and D. When one of them becomes larges, the other becomes smaller, and their combination remains the same. However, the impedance between the driven electrode D and the sensing electrode S1 is different when material is in two different positions, because the fringing electric field, shown as a dashed arc, has a limited penetration depth (which is a taught to be a function of the spacing between the electrodes). In the arrangement shown in FIG. 6c, the fringing electric field does not change due to the presence of object between the electrode plates. By analyzing different patterns of electric fields, one can determine both the composition and the position of the contraband material.

Figure 7:
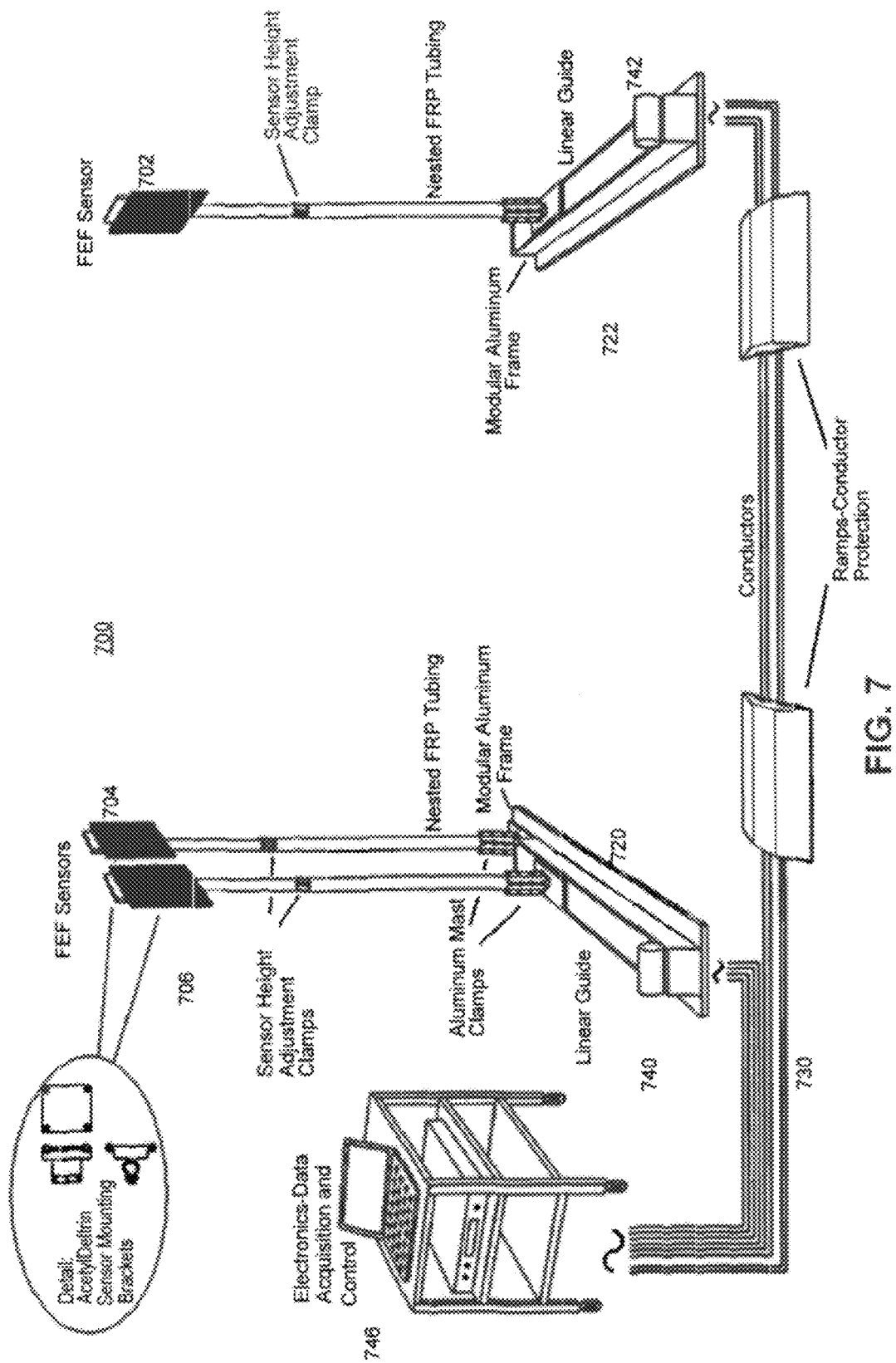
FIG. 7 is a schematic diagram of an arrangement for inspecting for an unknown target material. Electrodes assemblies are mounted to be movable along motorized tracks and are configured and arranged to implement fringing electric field and parallel-plate sensing. The movable electrodes enable producing fields of varying penetration depth.

FIG. 7 schematically represents a hardware arrangement 700 according to an embodiment of the invention. The embodiment shown in FIG. 7 is a custom dielectric measurement system. Hardware arrangement 700 is suitable for measurement for detection of materials inside of an enclosure not shown), according to the "reduced order" tomography approach using a simple RC forward model. A motorized dielectrometry system is fitted with an automatic multiplexer that allows measurements to be made in both fringing field and parallel plate modes. Electrode structures 702, 704 and 706 allow measurements to be made in both fringing field and parallel modes. Electrode structure 702 is attached to a linear stage 722. Electrode structures 704 and 706 are attached to a linear stage 720. A stepper motor 740 associated with linear stage 720 moves electrode structures 704 and 706 linearly back and forth along the stage. A stepper motor 722 associated with linear stage 742 moves electrode structure 702 linearly back and forth along that stage. Electrode structures 704 and 706 on linear stage 720 can be used to establish and sense a finging field for making variable penetration depth measurements, while driving electrode 702 moves on linear stage 722 enabling horizontal axis scanning. Conductors 730 connect electrodes 702, 704 and 706 with measuring instrumentation 746 which generates driving signals for the electrodes, receives signals from them and analyzes received signals.

FIG. 8a schematically depicts a top view of a hardware arrangement, such as, for example, the arrangement shown in FIG. 7, with an enclosure possibly containing a material of interest (illustrated as a vehicle without limitation) 802 positioned between stages 720 and 722. This sensor arrangement is capable of scanning the inside of a vehicle to identify one or more unknown materials. Measurements have been made of test materials in a measurement area inside of small sedan vehicle, which is parked between motorized stages 720 and 722. Measurements were made using the configuration of hardware generally shown in FIG. 8a with the following relative positions. The vehicle was positioned with about two feet of clearance between side walls of the vehicle and the electrodes. The distance between the electrodes and the sides of the test vehicle define the coupling and shielding capacitances, hence accurate information as to the position of the vehicle relative to the electrodes is critical. In this and other embodiments, this information is supplied using any of several distance measuring apparatus, including but not limited to a laser rangefinder.

Figure 8B:
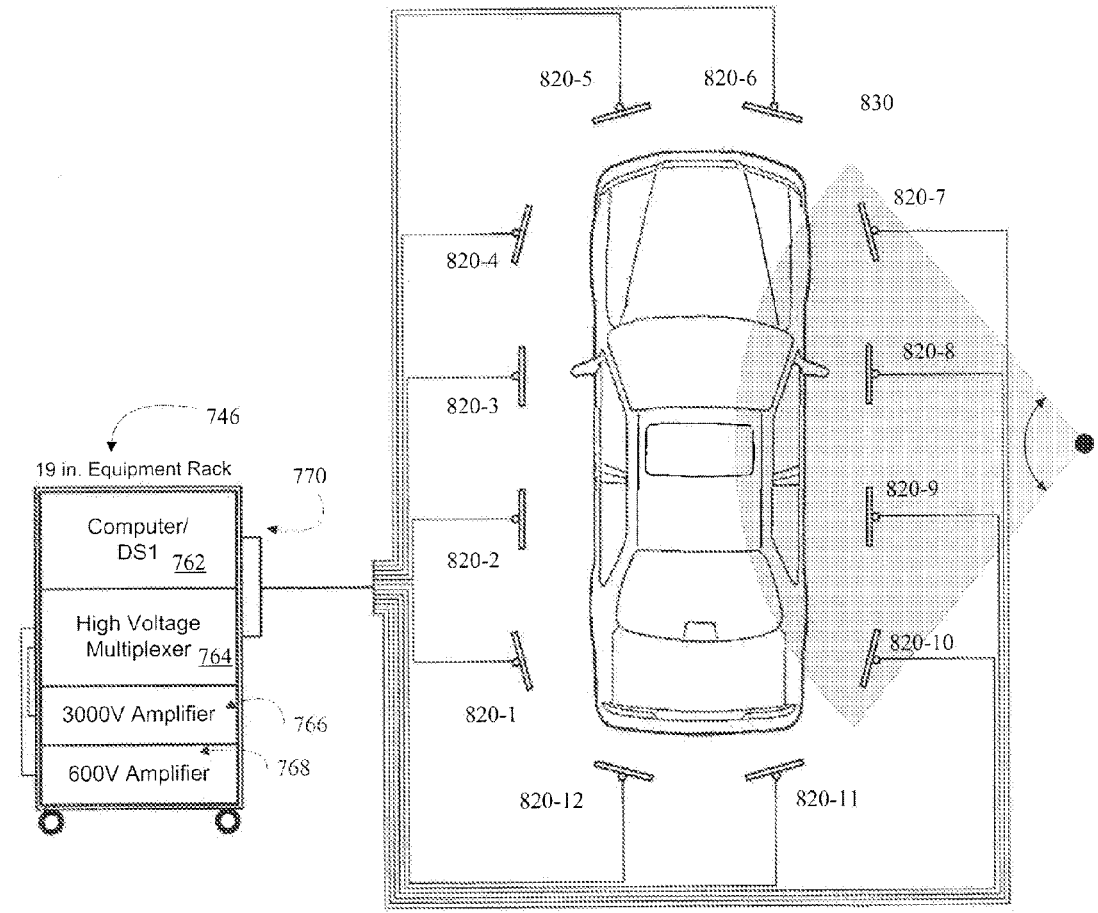

FIG. 8b depicts a top view of an embodiment of a test arrangement with eight electrodes 820-1 to 820-8 positioned around a vehicle 830 under inspection according to an embodiment of the invention. Measuring instrumentation 746 includes a computer 762, a high voltage multiplexer 764, a 300V Amplifier 766 and a 600V Amplifier 768, all stored in an equipment rack 770.

The electrodes in FIG. 8b are shown circumferentially around the test object, in a plane parallel to the ground. However, according to the invention these electrodes could be configured in any orientation, including circumferentially or any portion thereof, at staggered heights, and/or above or below the test object. Not all electrodes are necessarily energized or used; the pattern being determined by the size of the object under test, results of prior scans and other factors.

Instrumentation

Figure 9:
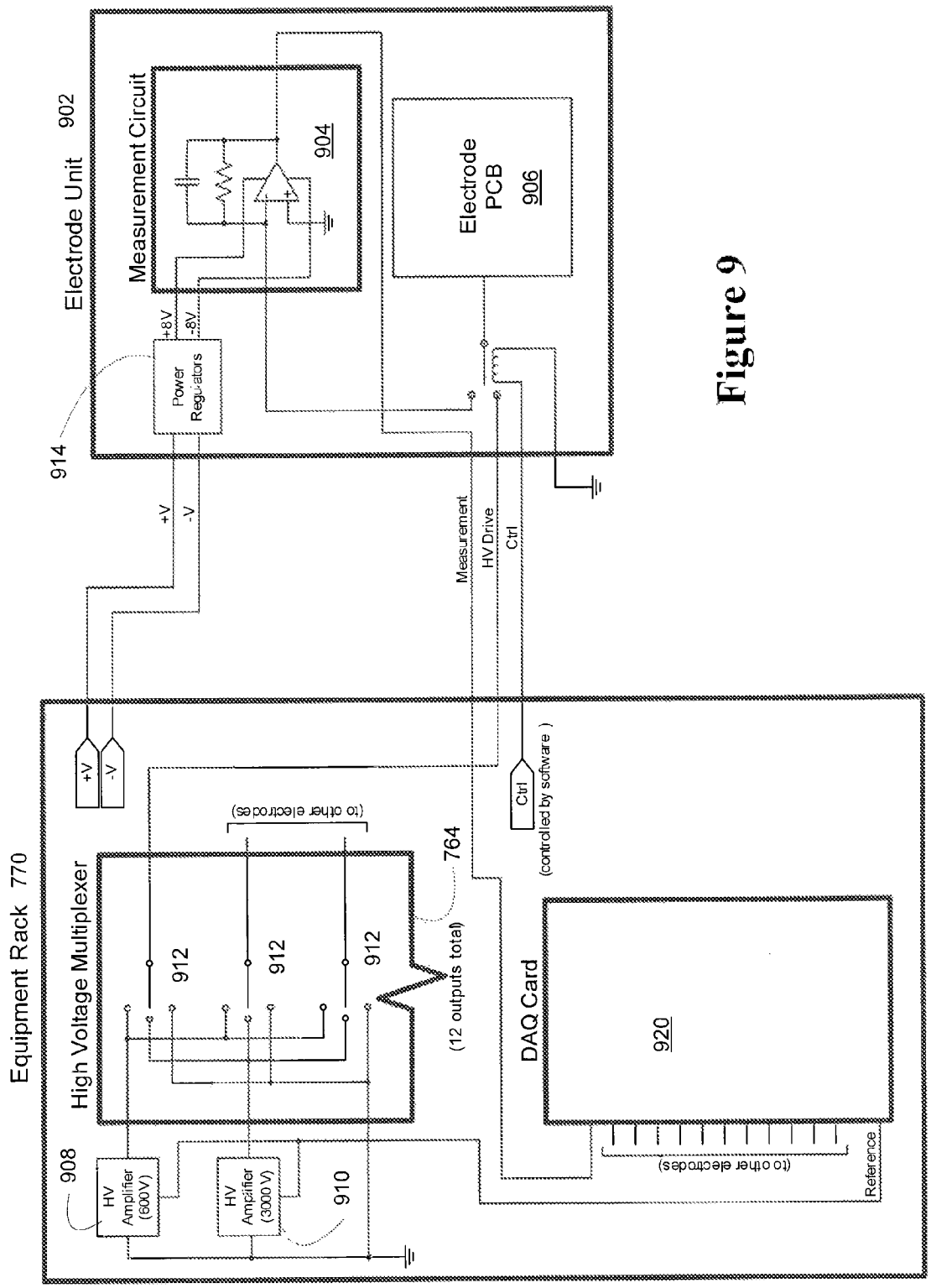
FIG. 9 is a schematic diagram of measuring instrumentation according to an embodiment of the invention.

FIG. 9 is a schematic diagram of an embodiment of measuring instrumentation 746 according to an embodiment of the invention. Equipment rack 770 contains large instrumentation elements of measuring instrumentation 746. An electrode unit 902 contains a measurement circuit 904 located close to the electrodes and the electrodes themselves, such as for example, electrode 906. A first high voltage amplifier 908 is in this embodiment a 600V amplifier. A second high voltage amplifier 810 is in this embodiment a 3000V amplifier. The first and second high voltage amplifiers provide amplification of a driving signal from several volts to several hundred volts. High voltage multiplexer 764 includes a set of relays 912 that select which of the high voltage multipliers is used. A power regulation unit 914 drops the high level driving voltage to the level convenient for measurement. The electrodes, such as electrode 906, are constructed by putting metal planes on a printed circuit board (PCB). Driven electrodes create the electric field used to interrogate an unknown material. A data acquisition card (DAQ Card) 920 acquires driving and sensing electrode signals for further processing, digitizes these signals, and sends the information to the computer.

Figure 10A:
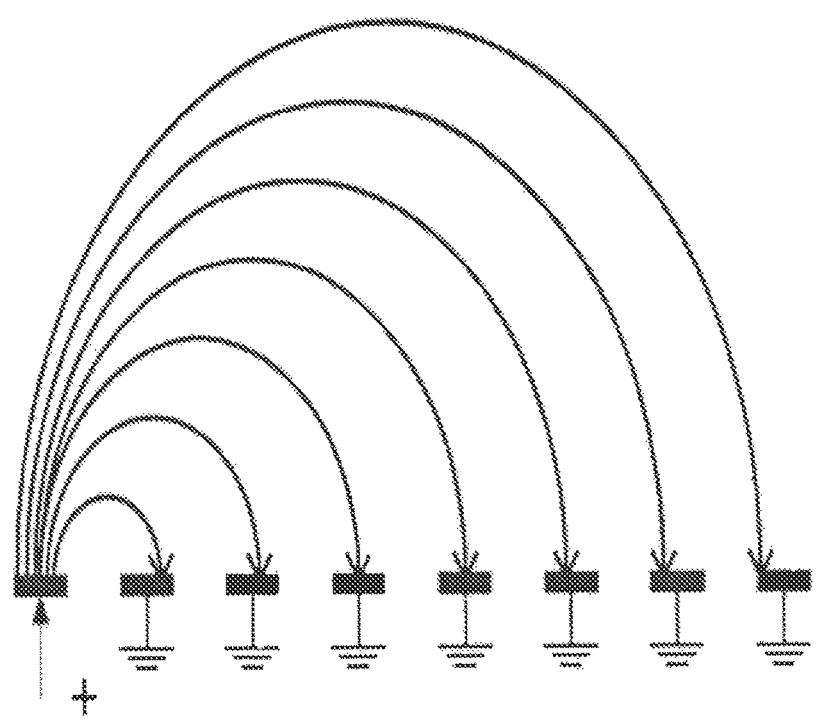
FIGS. 10a and 10b schematically depict a linear array of electrodes 1000-n and resulting field patterns. Each electrode can be switched to be either a driving or a sensing electrode.
Figure 10B:
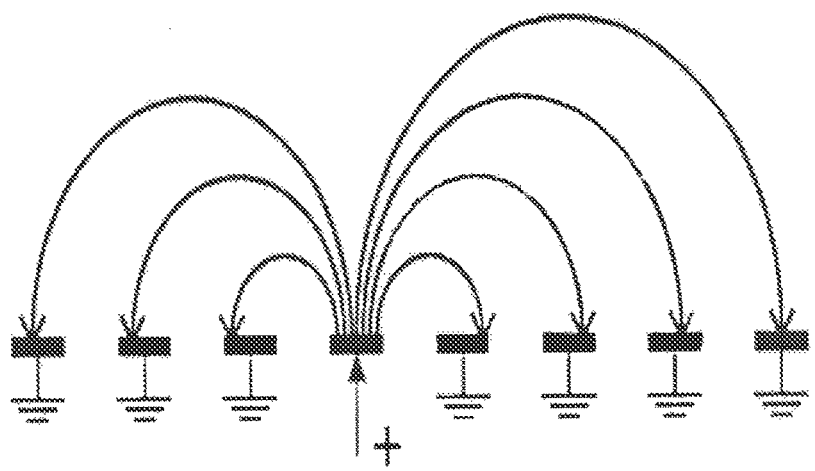

According to an embodiment, a user interface is provided that includes a console of controls and a display that allows an operator to determine various statuses and understand determinations made regarding the vehicle under test. Various methods are used to communicate to a human operator status and receive instructions regarding the carrying out of tests on the unknown material. The interface can display possible presence of a material of interest, uncertainty, and location of materials of interest. Short of a conclusive identification of a particular unidentified material a discontinuity in complex dielectric permittivity or other deviation may be suggestive of cached materials that requiring more thorough examination. One mode of display is an indication that to a predefined probability of detection and probability of false alarm, the presence of a contraband material was detected. Another mode of display would provide an indication that an unknown anomaly in the complex dielectric permittivity signature of the vehicle was detected that may bear further investigation. Yet a third mode of operation would be to synergistically fuse the complex dielectric permittivity signature with that of other sensing modalities to provide a possibly enhanced probability of detection and reduced probability of false alarm. The sensitivity of dielectrometry data is orthogonal to other sensing modalities commonly in use to detect and identify contraband materials, the fusion of dielectrometry with other bulk or trace detection methodologies evidence based reasoning approaches well known in the literature could enhance the detection of contraband. The use of an interactive user display provides an operator an opportunity to adjust measurement parameters via a keyboard during the inspection. For example, if the classification result is ambiguous, the operator could re-initialize the scan with different parameters according to the teaching of this invention. FIGS. 10a and 10b schematically depict a linear array of electrodes 1003, in which each electrode 1003-1 to 1003-n can be switched to be either a driving or a sensing electrode. When an unknown material under test is partially shielded, it is important to form the electric fields in such a way that the signal is most responsive to the changes of material properties inside the partially shielded region. This can be achieved by providing appropriate shielding around the sensing electrode, and orienting the electrodes with the side window apertures. In the example arrangement shown in FIG. 8a, the driven electrode, positioned on the opposite side of the car from the parallel plate sensing electrode, should be as large as the shielding areas plus the sensing electrode.

Figure 11:
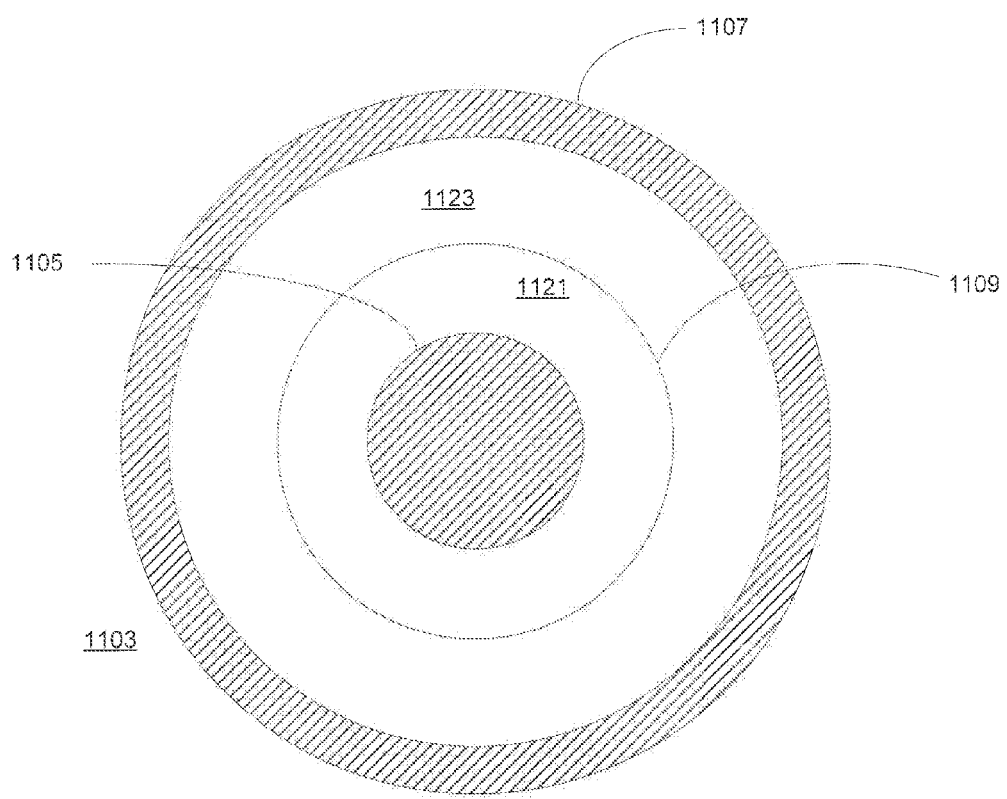
FIG. 11 is a schematic diagram of an arrangement of a co-axial conductor electrode arrangement useful for minimizing parasitic capacitance.

FIG. 11 depicts a coaxial cable 1103 with plastic spacers 1121 and 1123 separating an inner conductor 1105 from an outer conductor 1107 to reduce cable capacitance per meter length used in an experimental embodiment of the reduced order tomography dielectrometry system. When the distance between the sensing and driven electrodes is large, the capacitance of lead wires (wires that connect the electrodes to the measurement instrumentation 746) becomes significant. Where the electric field signal is usually delivered via a coaxial cable, such as, for example, coaxial cable 1103 (as opposed to another embodiment of the system wherein the excitation field is generated locally at the drive electrode), with the sensing signal being carried by the inner conductor 1105 of the co-axial cable. Regardless of the measurement circuit used, the potential of the outer conductor 1107 has to be the same as the potential of the inner conductor 1105. In a typical embodiment, short-circuit measurement scheme, the inner conductor is held at a virtual ground and the outer conductor at the actual ground reference potential. In order to keep the inner conductor at a virtual ground, current is fed to it via an amplifier circuit such as amplifier 908 or amplifier 910. The larger the parasitic capacitance between the inner and outer electrodes, the larger is the current that must be fed. Thus, if the length of the cable is too long, the parasitic capacitance is becomes too high, power supplied by the amplifier is insufficient to provide adequate amounts of current. In one embodiment, to reduce the capacitance of the cable per meter length, the outer electrode diameter is made artificially large, much larger than stipulated by the voltage insulation requirements.

Ordinarily objects subject to scanning (such as conducting shells) are effectively capacitively coupled to ground. For example, a vehicle's tires effectively provide capacitive coupling of the vehicle to ground. For certain measurement arrangements, it is advantageous to ground a conducting shell to the same ground as the measurement apparatus. In practice this results in higher signal levels being detected. In actual field measurements, such grounding can be carried out by using a probe that is grounded with measuring instrumentation 746. The inner conductor 1105 may be part on an insulated wire.

According to an embodiment of the invention, measurements are made of the impedance incidental to excitation by a variable frequency electric field. The invention exploits the broadband response of the "system" (e.g., vehicle plus contents) under investigation to determine if one of several different contraband materials is present above threshold quantities in the system. It has been observed that the maximum difference in the permittivity response of dielectric materials occurs at the lower excitation frequencies, since in practice a number of different measurements are averaged to obtain an average impedance measurement that is used to estimate the permittivity features of the materials under test, measurement latency can become an important parameter at low frequencies. Additionally, integration over larger number of cycles is not an open ended process; i.e., too much integration not only increases system latency, but can add noise that ultimately degrades the estimation of frequency dependent permittivity features and material classification.

Dynamic Adjustment of Data

Figure 12:
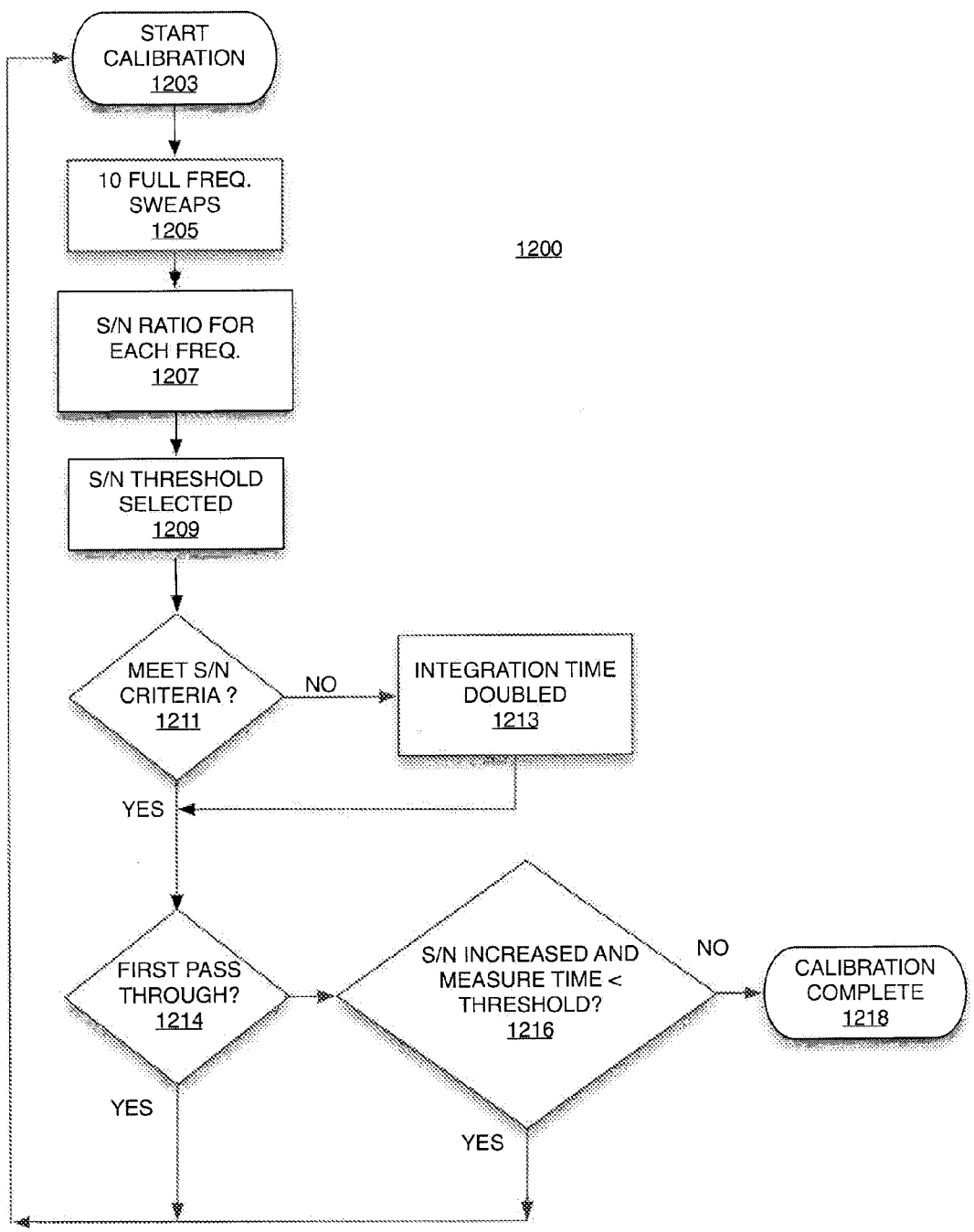
FIG. 12 is a flow chart describing a process for testing an unknown target material according to an embodiment of the invention.

FIG. 12 is a flowchart of an example process 1200 applicable to various embodiments of the invention. It explains a process to dynamically adjust the number of measured data points and the duration of time taken for measurement of each data point. Process 1200 is carried out in the following manner.

In a calibration process initiated at step 1203, optimum integration times are selected and the number of data points to be measured is selected. In a measurement process, measurements are conducted with the parameters selected during the calibration process. The following describes the calibration process: At step 1205, ten full frequency sweeps are acquired for a static measurement (nothing changes during the measurement series) with initial integration times for lower frequencies being equal to three times the periods corresponding to each frequency. At step 1207 a signal-to-noise ratio is calculated for each frequency. At step 1209 a signal-to-noise threshold is selected so that more than half of frequencies are considered satisfactory. For the low frequencies for which the data does not meet SNR criteria, the integration time is doubled at step 1213. Steps 1 to 4 are repeated.

If the resulting SNRs have improved (increased) and the total measurement time is still below the threshold time, then steps 1 through 5 are repeated. Otherwise, the calibration is complete and optimal integration times are recorded. After the calibration process is complete, the measurements are made. The permittivity signature of materials that comprise only a small fraction of measurement volume manifest themselves as small perturbations of a larger baseline signal. In order to better characterize these perturbations, the current invention and its several embodiments uses the same amplification stage for every data point. The current invention chooses signal amplification level so that the resulting signal is always within the dynamic range of the digitizing circuit which digitizes the measured results.

A vehicle under test is positioned between two rows of electrodes (as shown in FIG. 8*b*). When the electrodes are positioned along two parallel planes, an electric field generated by those electrodes is concentrated primarily in a region between the electrodes. An embodiment of the invention uses shielding on the electrodes to a) increase the ratio of capacitance change due to the presence of material under test to the capacitance between the electrodes and b) minimize noise from objects moving outside of the measurement area will be minimized.

Figure 13:
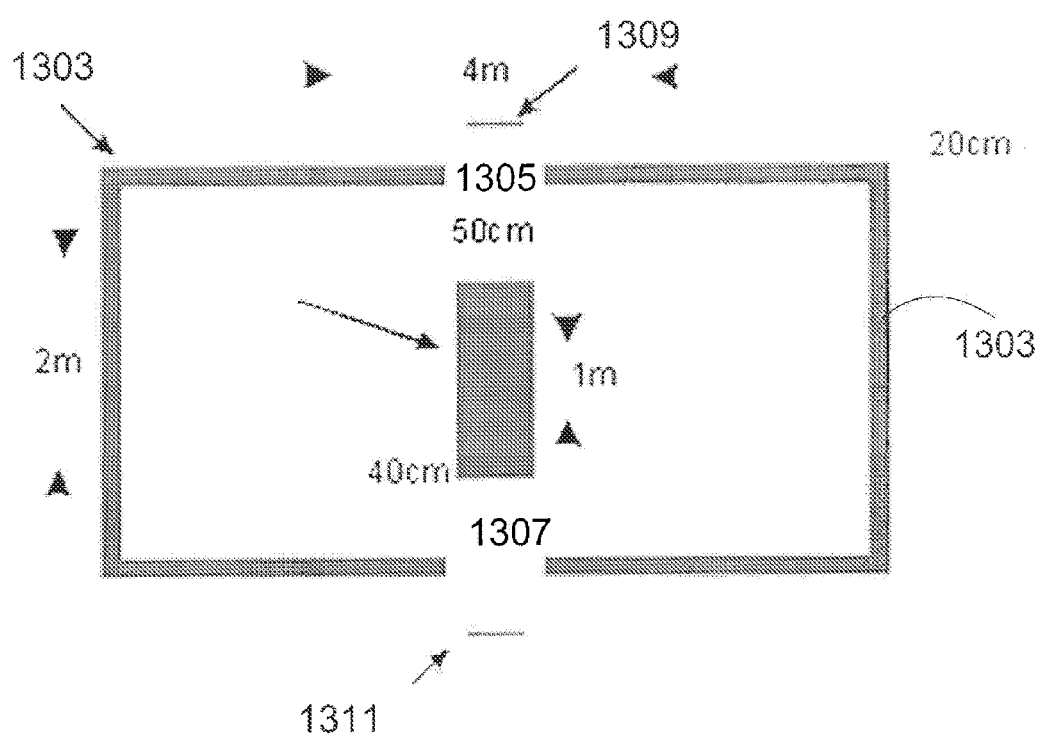
FIG. 13 is a schematic representation of an electrode arrangement particularly useful for focusing of an electric field inside a vehicle that may contain a target material to be identified.

FIG. 13 is a schematic representation of an electrode arrangement allowing focusing of an electric field inside a vehicle. The figure schematically shows a two-dimensional representation of an electrically conductive object (vehicle) 1303 with windows 1305 and 1307, electrodes on the outside (driven electrode 1309 and sensing electrode 1311) and material under test 1313 inside the vehicle.

Figure 14:
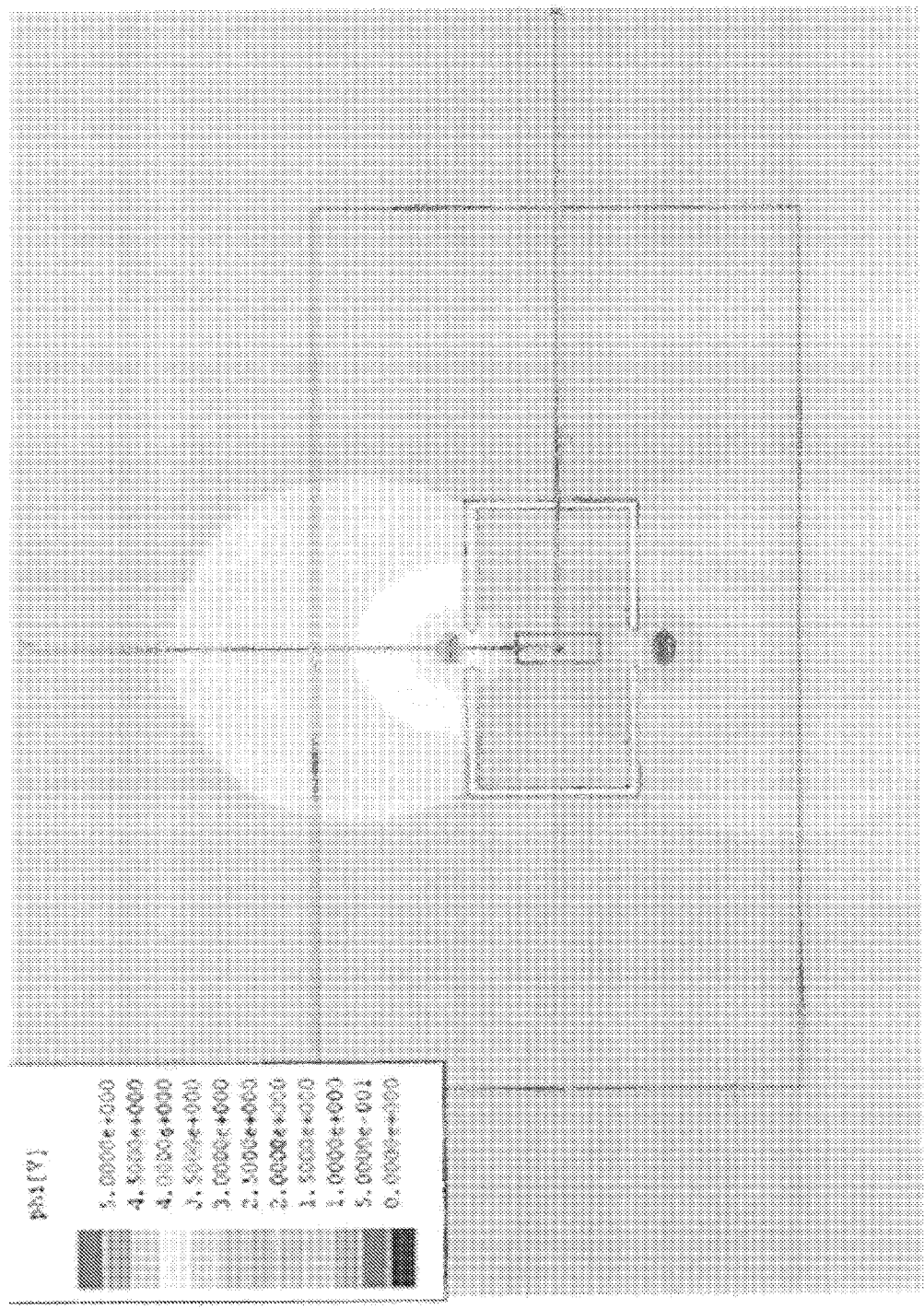
FIG. 14 is a graphical representation of equipotential electric field lines resulting from use of the electrode arrangement shown in FIG. 13.

FIG. 14 is a graphical representation of a distribution of equipotential lines for the electrode arrangement shown in FIG. 13. For the case where the electrodes are not shielded, the distribution of equipotential lines is as shown in FIG. 14. A much higher potential exists outside of the conducting object rather than inside, although the electric field does penetrate through the apertures.

Figure 15:
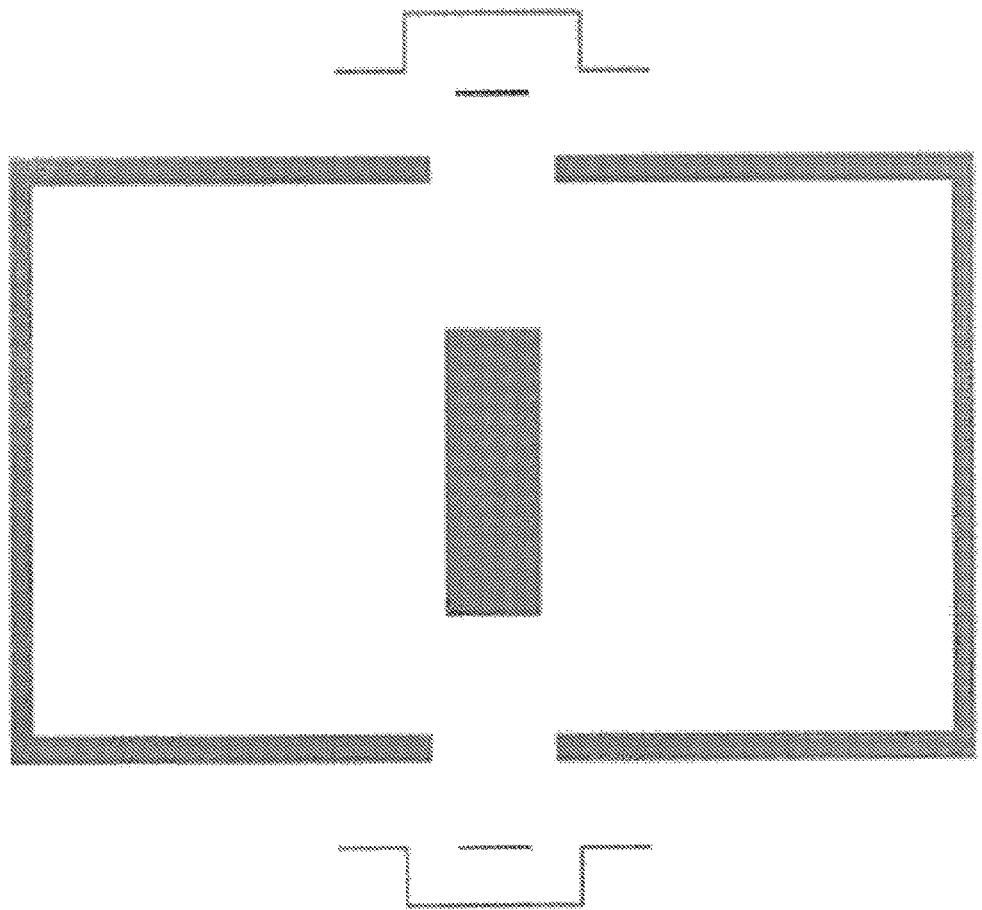
FIG. 15 depicts an electrode arrangement similar to that shown in FIG. 13 but including shielding on the outside of both driven and sensing electrodes.

FIG. 15 is a schematic diagram of an electrode arrangement similar to that shown in FIG. 13. However, in FIG. 15, shields 1503 and 1505 have been added surrounding respective electrodes as is taught in the current invention.

Figure 16:
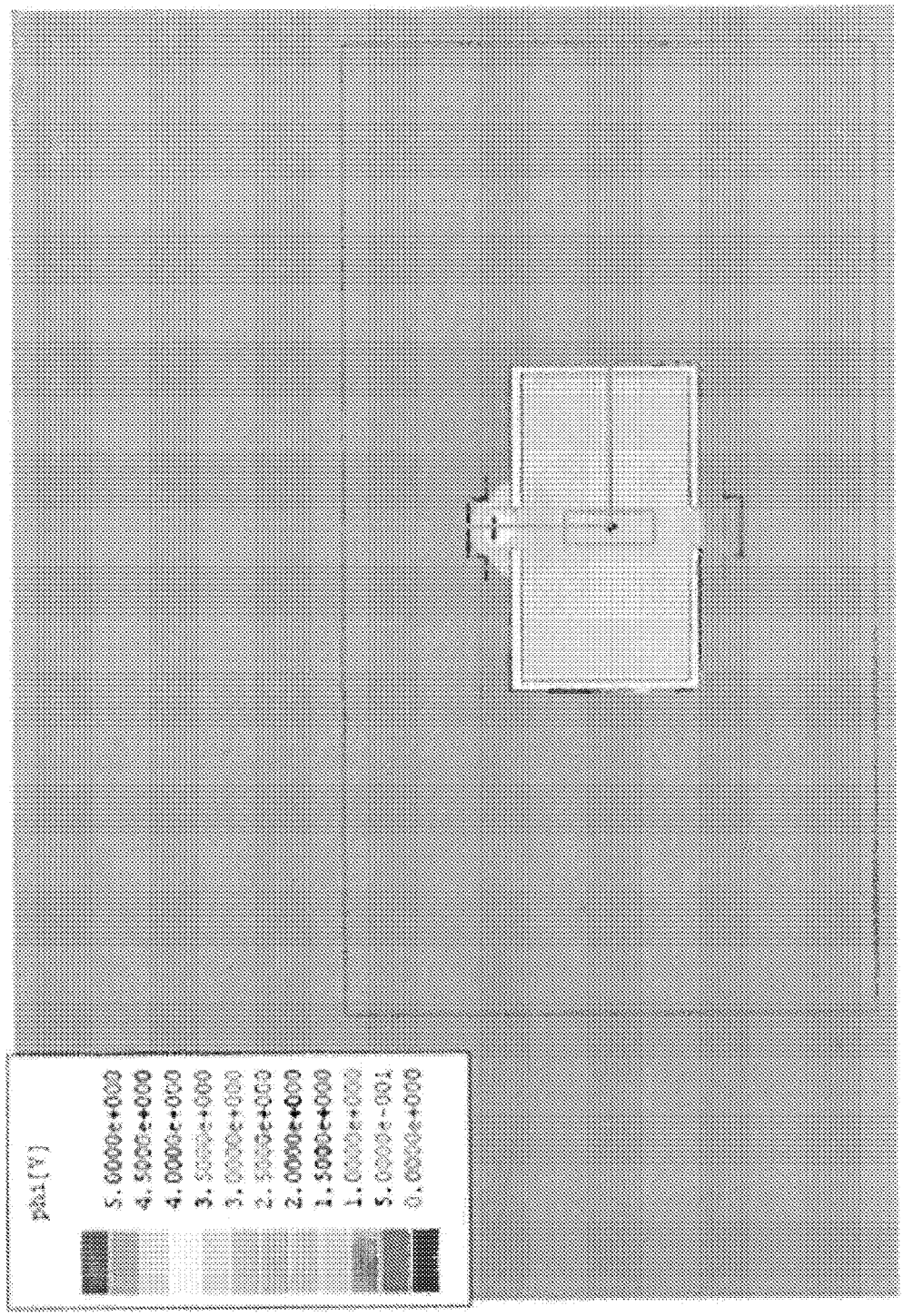
FIG. 16 is a graphical representation of equipotential electric field lines for the shielded electrode arrangement shown in FIG. 15.

FIG. 16 graphically depicts a distribution of equipotential lines for the arrangement shown in FIG. 15. The electric field in the conducting object, where the material of interest is located is now stronger than the electric field outside of the object. Therefore, changes in properties of the material under test will register better in the latter case. More specifically, a sensitivity improvement by a factor of about 3 (0.13/0.04) is realized with the addition of shielding, as long as an analog to digital converter used in measurement has a sufficient resolution for the weaker signal magnitude for the shielded arrangement.

In addition to shielding, embodiments of the invention exploit the distance between the electrodes and the body of the container package. The presence of large metal objects (electrically conductive objects) in the field of sensing results in significant changes of impedance measured between the remotely positioned electrodes due to minor variations of their positions. In order to eliminate this effect, embodiments of the invention employ a distance measurement device, such as but not limited to a laser or ultrasonic ranger finder installed next to the electrodes, and the distance information is used to compute the coupling capacitances, making dielectric signatures more accurate.

Measurements presented thus far were made for the most part by varying an AC excitation field sequentially from a highest excitation frequency to a lowest excitation frequency as voltage potential measurements were made. In embodiments of the invention, these impedance measurements are inverted to achieve material classification.

Two or More Excitation Fields

It has now been determined that two or more excitation fields may be simultaneously applied to a material under test to advantage. Simultaneously applying two or more fields speeds the process of scanning and identifying unknown materials. It can, for example, identify and in some cases induce anisotropic response in a material of interest to enhance classification.

Figure 17:
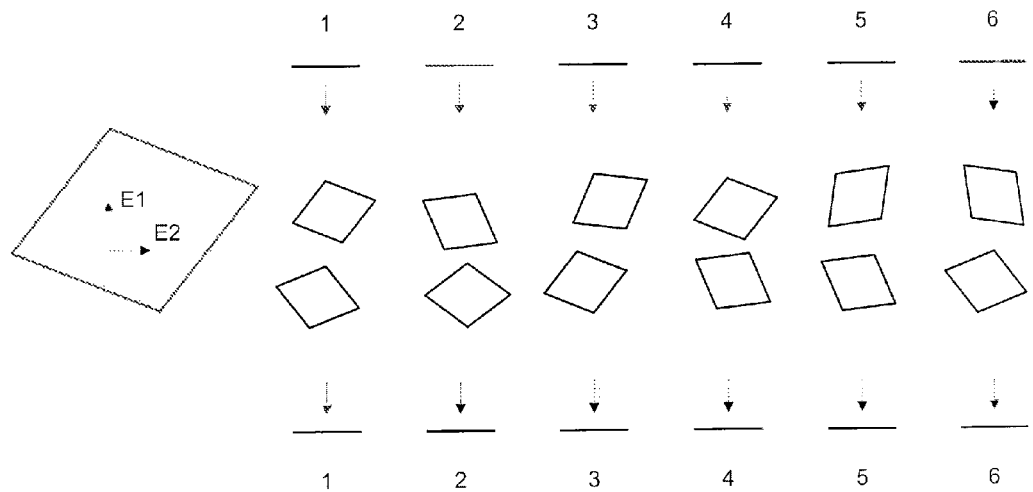
FIG. 17 is a schematic representation of a crystal with anisotropic dielectric permittivity, and a multi-electrode measurement arrangement that uses anisotropy as a material identification feature.

For certain contraband materials and other materials of interest that are in a crystalline form, an anisotropic permittivity response may be observed. FIG. 17 schematically depicts a crystal with anisotropic dielectric permittivity. A multi-electrode measurement, for example, with electrodes positioned circumferentially around the object under test, such as shown in FIG. 8*b*, can utilize this anisotropy to advantage in distinguishing between materials to be identified. A globally applied field measures average dielectric permittivity, and a small area through-field pattern shows that a dielectric permittivity in a certain direction is different from average dielectric permittivity. Combined with other features, exploitation of this material feature in the current invention could enable better detection of substances of interest.

Pre-processing of Signals

One important characteristic of dielectric signatures is that when the separation between the electrodes is comparable to electrode size or larger than the electrode size (as in the case of measurements with a vehicle), acquired signals are very weak, and, consequently, signal-to-noise ratio (SNR) is low. Preprocessing signals applied in the invention overcomes this problem.

There are several preprocessing steps implemented in the invention and its several embodiments. The first of these preprocessing steps is data normalization. Other preprocessing steps that are applicable to embodiments using higher order tomographic approaches are discussed later.

Permittivity measurements drift over ambient temperature, temperature of the detection circuits, and other factors which are reflected in the data as time dependent drafts. In order to exploit the permittivity data it is necessary to normalize the readings so that a particular material yields consistent results. This makes classifying a run (i.e. deciding what its material is) easier.

Certain normalization methods found in the literature have proven to be of limited help in classification, while others implemented in the current invention have proven to be more helpful in extracting permittivity data. For example, two previously utilized normalization methods, namely subtracting the capacitance values of the nearest air run point-wise from the capacitance values of the material run, and dividing the capacitance values of the material run point-wise by the capacitance values of the nearest air run, provides only limited success in clustering and classification accuracy. An alternative normalization process found in the literature is to divide each run's data vector by the capacitance value (at the chosen frequency) of the nearest air run. In this case the normalized values are again ratios, but the values at the chosen frequency are not equal to "1".

According to the invention and some of its embodiments, two (2) frequencies are chosen and the data normalize by each (separately), and use both resulting vectors in the classification process. This prevents the data at the chosen frequency being lost.

Given a collection of data vectors (in particular, permittivity measures such as capacitance readings for various materials at a set of frequencies), it can be assessed how well a normalization functions by evaluating: 1) how well normalization compensates for various forms of experimental noise and 2) how well the different materials cluster or group.

One approach to assessing clustering is to use a root mean square (RMS) metric, measuring the range of data variation at each index of the normalized data vectors. Given a collection of m-point data vectors $\{Vi\}$, where $Vi=\{Vi1, Vi2, \ldots Vim\}$, RMS is defined as $$RMS(V_i) = \sqrt{\Sigma(max_j - min_j)^2}$$

where for each j, $max_j$=max of all data values at frequency j and $min_j$=min of all data values at frequency j.

The smaller the number RMS, the more closely the vectors cluster. In an extreme case, if the normalization stacks all vectors exactly on top of one another, the RMS value will equal zero. In our tables of clustering data we scale all values for ease.

This metric measures total spread at all frequencies, and is sensitive to "outliers". That is, if all vectors cluster except for one, the RMS will be the same as if the vectors cluster loosely, but with the same outer bounds. If the vectors cluster well at all frequencies except one or two, these aberrant frequencies will increase the RMS value.

Again assuming a collection of m-point data vectors $\{V_i\}$, where $V_i=\{V_{i1}, V_{i2}, \ldots V_{im}\}$, associated with several materials it is desirable to know from which material a particular unknown data vector originates. In particular, we wish to assess how accurately we can classify a normalized set of vectors, in order to assess the effectiveness of the normalization. There are many methods for classification reported in the literature, including k nearest neighbors, support vector machines, neural nets, partial least squares, manifold learning and other techniques. These methods vary in complexity, robustness to noise and suitability to classification of permittivity data. The properties of dielectric spectra complicate the classification process. The classifier must handle very broad features whose locations are not fixed. An additional complication is that the features in many cases were found to lie at the edge of the measurement range. The process begins by extracting from the data a set of features that capture some of the invariants in the data.

According to an embodiment of this invention a kNN classification algorithm is used, however dozens of classification and pattern recognition algorithms with or without dimensionality reduction are well known in the art and could be employed according to the teaching of the present invention to dielectrometry data. In the kNN algorithm "k" refers to the number of nearest neighbors we will poll (as explained below). We begin with a set of normalized data vectors. Their classes (e.g., materials of origin) are known. Treating each vector in turn as the unknown vector, we measure a "distance", Dist ( ) from this vector to each of the other vectors in the set. In one embodiment of the invention we define distance as:

$$Dist(U,V_i) = \sqrt{\sqrt{(U_j - V_{ij})^2}}$$

where U is the selected "unknown" vector, and $\{Vi\}$ are all the other vectors in the set. Another variant used in the invention, combines data vectors from two distinct normalizations. These vectors are simply concatenated to make a data vector twice as long. Then Dist ( ) sums from 1 to 2 m (if using all frequencies), where m is the length of the original data vector. The algorithm selects k vectors closest to the unknown vector, according to the defined distance metric. These k vectors are known in the art as the polling group. The classification (material of origin) of these vectors is known. We take the majority vote of the classes of this group, and classify the unknown vector to be this type. For example, if the 3 nearest neighbors of a particular vector were {material A, material B, material A}, that vector would be classified as "material A". Note that odd k are more likely to give unambiguous results (because of fewer ties), especially if there are only a few classes.

For even values of k it is possible to resolve voting ties by comparing $\{Dist (U,V_i)\}$ for all vectors involved in the tie. The class of the unknown vector is defined to be the class of the vector with minimum distance. Using different values of k can result in different classifications of a particular vector. In general, the best values of k will depend on the number of data vectors and how they are distributed. For example, if there are 20 data vectors, 5 each from 4 materials, with each material type relatively tightly clustered, a value of k greater than 4 will likely give worse results, because k>4 guarantees that we include vectors of different class (from our unknown vector) in the polling group, increasing the chance of an inaccurate vote.

Enhanced Tomographic Inversion

Some embodiments of the invention utilize a reduced order tomography process. One example of this reduced order tomography process includes the use of a single parallel RC circuit forward model. Although this method can be used over a limited range of operational conditions, the assumption that the system under test (e.g., vehicle with multiple materials present inside its conducting metal shell) can be modeled as a single parallel RCL circuit limits resolution and accuracy. A further embodiment of the invention combines a higher order forward model with a tomographic inverse method and customized classification algorithm that more completely captures the relevant physics and to produce an operationally robust process for both improved material classification and determination of material location within a vehicle.

Figure 26:
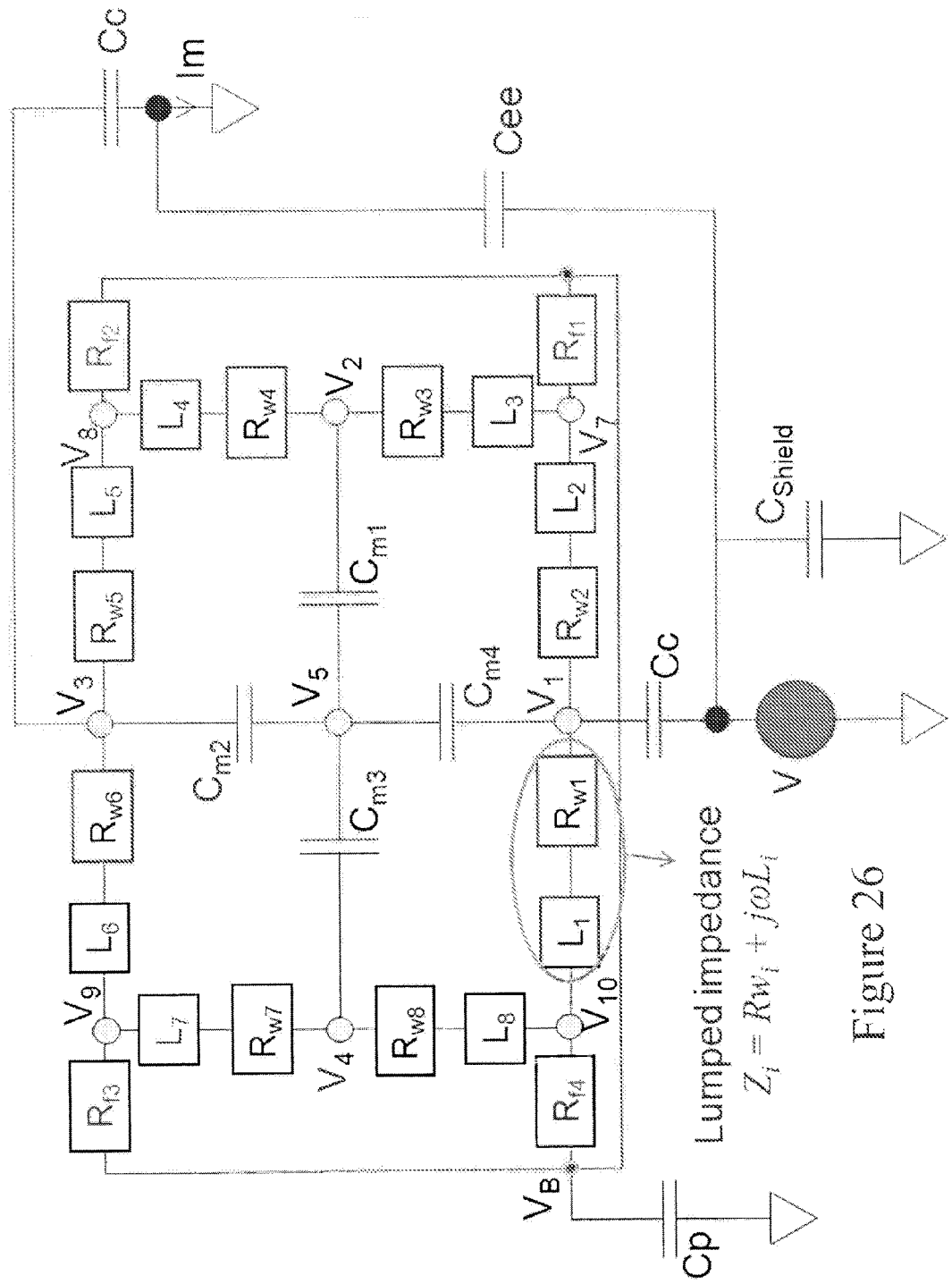
FIG. 26 is an equivalent circuit diagram of a representative forward model (shown as block FM in FIG. 1) used in embodiments of the invention.

More specifically, there is now disclosed a lumped linear equivalent electrical circuit forward model based tomographic method and a customized classification process based on any of several analytic processes, including diffusion geometry. The response of the material of interest, the distortion of the electric field by a vehicle and its contents, and the geometrical relationship between the multiple electrodes and the vehicle are now represented using a lumped linear equivalent electrical circuit forward model. An example representative electrical circuit schematic model is shown in FIG. 26.

In contrast to the simple RCL circuit approximation outlined in a previous embodiment, in this model vehicle shielding effects present themselves as low impedance resistive elements at locations corresponding to the vehicle body and frame. The contents of the vehicle are characterized by material properties, represented as capacitances and resistances that have values proportional to their (possibly frequency dependent) relative dielectric constant and conductivity. Coupling effects of the field between the drive and sense electrodes and the vehicle, and between the drive and sense electrodes themselves and the surface supporting the vehicle, are represented by coupling and parasitic capacitances respectively.

A tomographic method according to an embodiment of the invention is self-calibrating in the sense that a representative circuit topology that does not require detailed a priori knowledge of the vehicle being interrogated, is utilized, in contrast to the reduce order tomographic embodiment discussed previously. For an exemplary test arrangement wherein N electrodes are employed this method uses the N*(N−1) unique trans-impedance measurements obtained at each frequency as input data. Equivalent circuit element values are selected by an inversion process that optimally matches predictions from the lumped linear equivalent electrical circuit forward model with currently measured trans-impedance data related to a vehicle or other object under current inspection. While the system model is linear from an input-output perspective, the system identification problem, where given pairs of input-output data we need to determine the system parameters, is highly non-linear. Accordingly a known gradient search process is used to determine element values that best match the measured trans-impedance data.

Other embodiments of the invention employ higher order tomographic models. Constraints on classification the associated apparatus are considerably more complicated than the apparatus described for the reduced or tomographic system. In the higher order tomographic system N different bi-modal sensors are positioned around the object under test, in the case of a vehicle, sensors may be positioned front and back in addition to the right and left side but also may be of stagger height, above and below the object to be scanned. These sensors include the cascade of low-voltage signal amplifiers, relays, multiplexors, electrodes on electrode stands and cabling, two-range high voltage amplifier, a laser distance profile measurement system, and a high-frequency analyzer. The laser system or other distance measuring apparatus measures distances between an object being scanned and electrodes. In the case of a vehicle, it measures the contour of the vehicle body, position of windows, etc. Electrodes may be positioned at vehicle windows. Contours of vehicles and window positions are maintained in a vehicle database linked to make and model of the car. The database advantageously includes measurements of empty vehicles and cars with one or more occupants and common—no contraband—objects for each make and model. This would be used by the tomography process.

The electrodes in the higher order tomography embodiment could take any of several different forms, including square, concentric rings and interlaced fingers. Some or all of the electrodes will be configured to allow adjustment to the size and shape of the object under test. Each sensor may serve as a sense or drive electrode. The invention contemplates a protocol wherein sensors positioned proximate to the object to be tested are driven either round robin or in some other sequence. As in the case of the reduced order embodiment, each of the drive electrodes provide for a scan across a wide range of frequencies. Since the information content of the permittivity signatures is contained in the broad band response, in this embodiment we contemplate an expanded operating frequency range. The use of higher operating voltages can provide greater signal to noise.

An embodiment of the invention including a full tomography measurement system will be described. The measurement system has a number such as 12 measurement channels, each having a shielded electrode. Each electrode is configured for dual purposes, namely it can be excited as drive electrode or it can function as a sense electrode. Electrodes can be either stationary or movable during interrogation. For example, the electrodes can be mounted on movable tracks, as in other embodiments of the invention described herein. Alternatively the electrodes can be switched to provide the differential geometry. This embodiment is well suited for interrogating for unknown substances in a vehicle and it will be described for use with a vehicle for convenience of explanation. However, it is applicable to other search purposes as well, including buildings, boxes, and other "containers" regardless of scale or application. With automatic or manual adjustment it is possible to accommodate the variety of vehicle sizes. The electrodes can be positioned around the vehicle in various configurations. For convenience of description, this embodiment is described with an electrode arrangement including two to four electrodes on each side of a vehicle to be searched. Other numbers of electrodes and arrangements of electrodes can be used and are consistent with the invention. For example and without limitation, electrodes can also be positioned in the front or hack of the vehicle, or below (as in on or embedded in the road surface) and above the vehicle.

Figure 18:
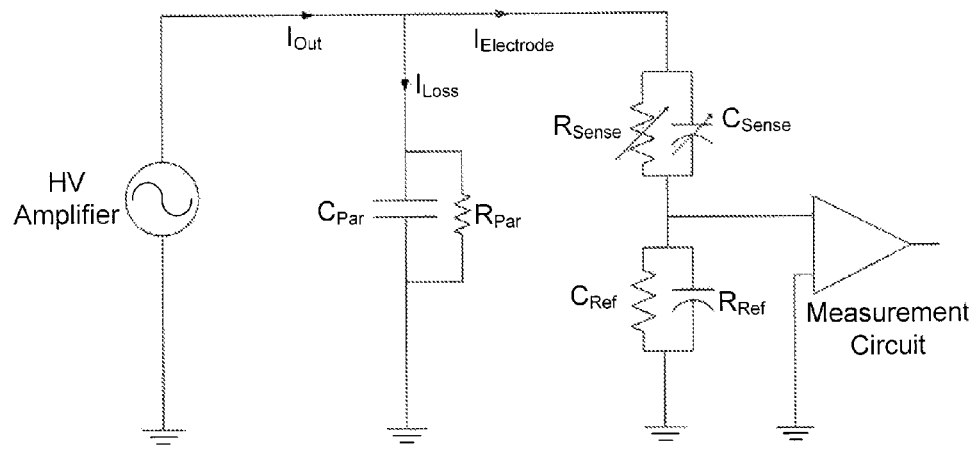
FIG. 18 is a schematic diagram of an electrical equivalent circuit of cabling and electrodes of a full tomography embodiment of the invention.

FIG. 18 is a schematic diagram of a simplified electrical equivalent circuit showing the effect of cabling and electrodes for this embodiment. To preserve fidelity of signals and to accurately measure phase differences between drive and sense signals, hardware timed high resolution digital to analog converters are used both to generate drive signals and to digitize sense signals. Drive signals are amplified by one or more high voltage amplifiers, outputs of which are applied to drive electrodes.

For safety, and to prevent electromagnetic noise from being introduced into the system, the high voltage cable connecting the amplifier and the electrode is cased in a flexible metal conductive conduit. By enclosing the cable in a conductive conduit, parasitic impedance between the drive signal and ground (CPar and RPar) is introduced. As the length of the cable increases, the loss due to the parasitic impedance (Iloss) increases thereby increasing the amplifier's output current (Iout).

$$I_{Out} = I_{Loss} I_{Electrode} \qquad (1)$$

Therefore the maximum length of the cable connecting the amplifier and the electrodes is limited by the output current capacity of the amplifier. In this embodiment a sensor is placed alongside the window of the vehicle. The cable must have adequate slack for sensors to move back and forth to accommodate for opening of a vehicle door.

Figure 19:
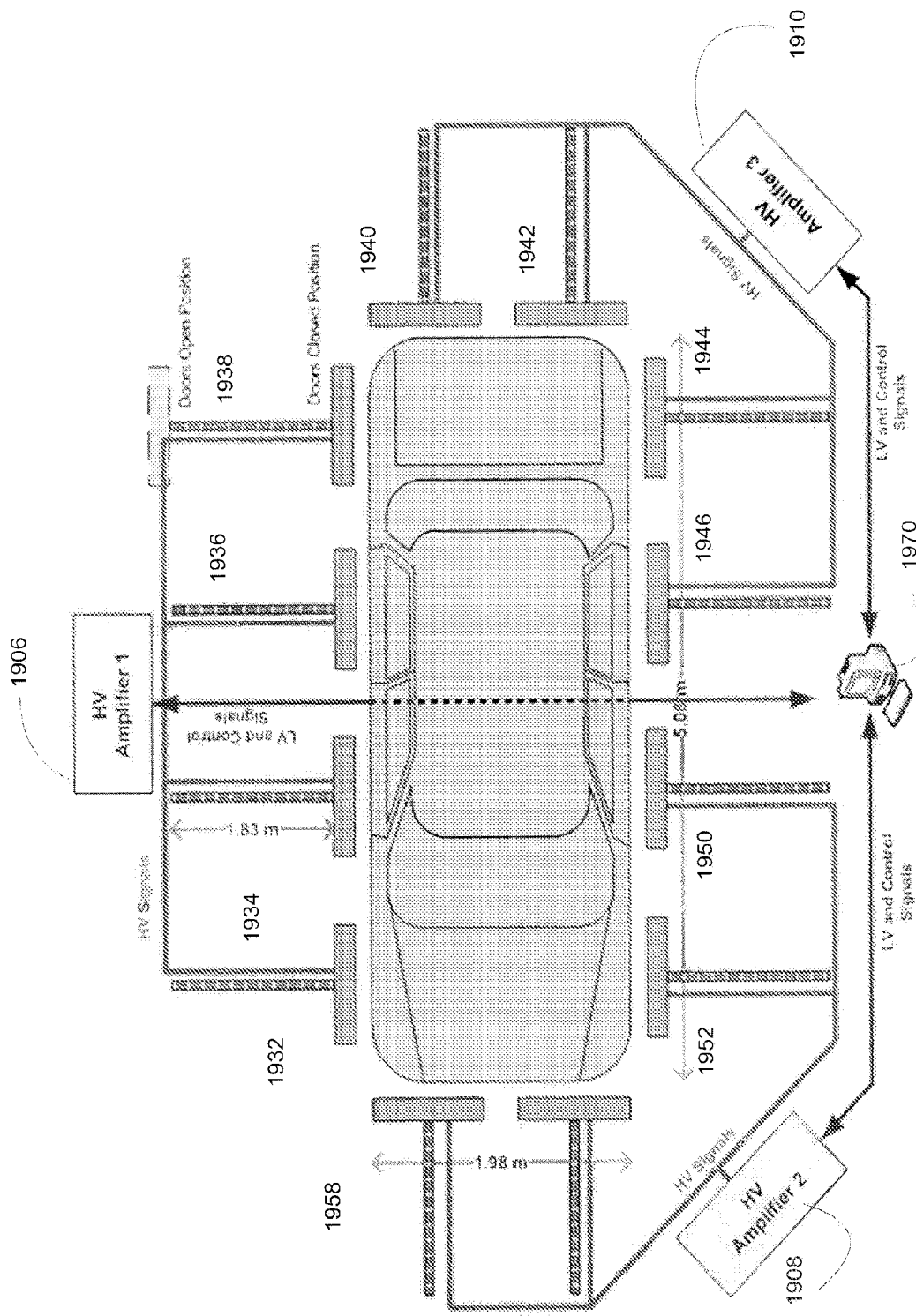
FIG. 19 is a schematic diagram showing an arrangement of electrodes, instrumentation, and cabling for an example maximum cable length of 6.25 m according to a full tomography embodiment of the invention.

FIG. 19 is a schematic diagram showing an arrangement of electrodes, instrumentation, and cabling. In this particular example, the instrumentation permits a maximum cable length of 6.25 m. It shows an optimal layout of system elements with the afore-mentioned design constraints. The system includes three banks of amplifiers including amplifiers 1906, 1908 and 1910 and instrumentation, each of which is connected to four electrodes. Amplifier 1906 is connected to electrodes 1932, 1934, 1936 and 1938. Amplifier 1910 is connected to electrodes 1940, 1942, 1946 and 1948. Amplifier 1908 is connected to electrodes 1950, 1952, 1956 and 1958. A low voltage signal generated from a central computer 1970 along with control signals controls operation of the instrumentation banks.

In order that each electrode can function as both a drive electrode and a sensing electrode, signal lines connecting the electrodes and the electronics can include two pairs of cables, each being optimized for drive and sensing modes, respectively.

An alternative embodiment uses a single cable that is multiplexed using a switching network to function in both modes. Physically the cable bundle remains the same. A co-axial cable is run through au interior space of a metallic conduit and provides three conductive paths between the electrodes and the instrumentation. These paths carry different signals in each of the operation modes as tabulated in Table 1 which describes signals carried by the conductors in the cable bundle in drive and sense modes.

TABLE 1

| Conductor | Drive Mode | Sense Mode |
| --- | --- | --- |
| Conduit | Ground | Ground |
| Cable Conductor | Drive Signal to Electrode | Sense Signal from Electrode |
| Cable Shield | Drive Signal to Electrode | Ground |

Figure 20:
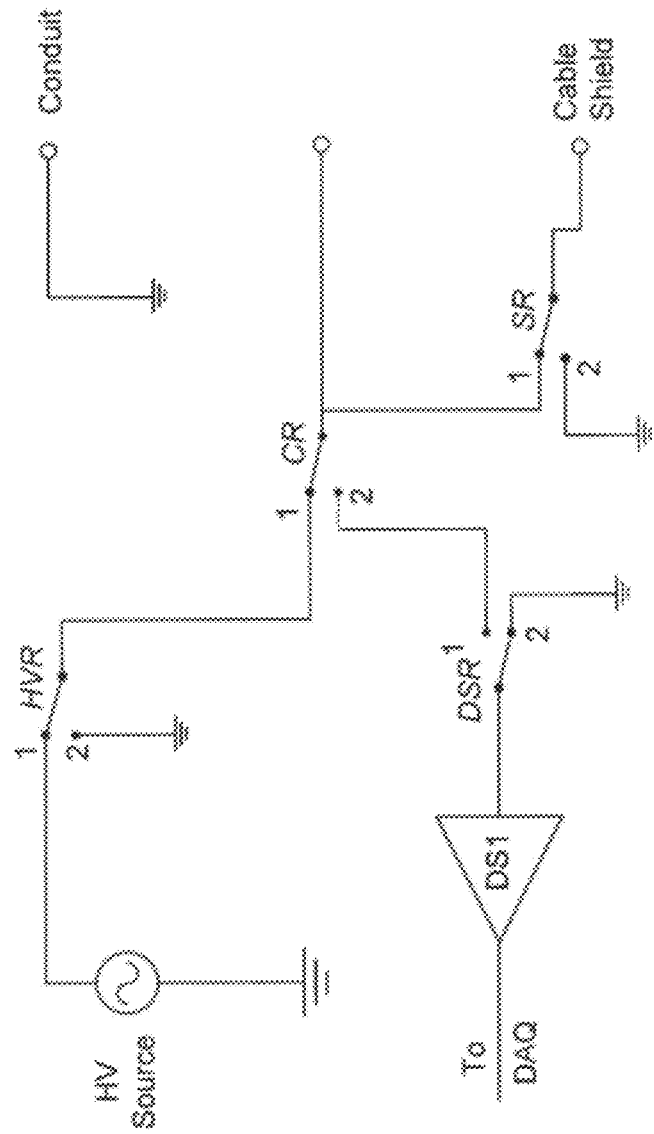
FIG. 20 is a schematic diagram of a switching network to multiplex cables implemented using SPDT relays of a full tomography embodiment of the invention.

FIG. 20 is a schematic representation of an alternative embodiment illustrating one way to implement multiplexing capability using a set of four SPDT relays. In drive mode, the cable conductor and shield are connected to the HV source through relays high voltage relay (HVR), conductor relay (CR) and shield relay (SR). Since most relays have significant capacitive coupling between the terminals even if they are not connected, the measurement system will be overwhelmed by the HV signal that leaks over CR unless it is grounded through DS1 protection relay (DSR). In the sense mode, the cable conductor will be connected to the measurement circuit through DSR and CR, while the cable shield is grounded through SR. To prevent the HV source from introducing noise in to the system, the cable connecting HVR and CR is grounded.

Figure 21:
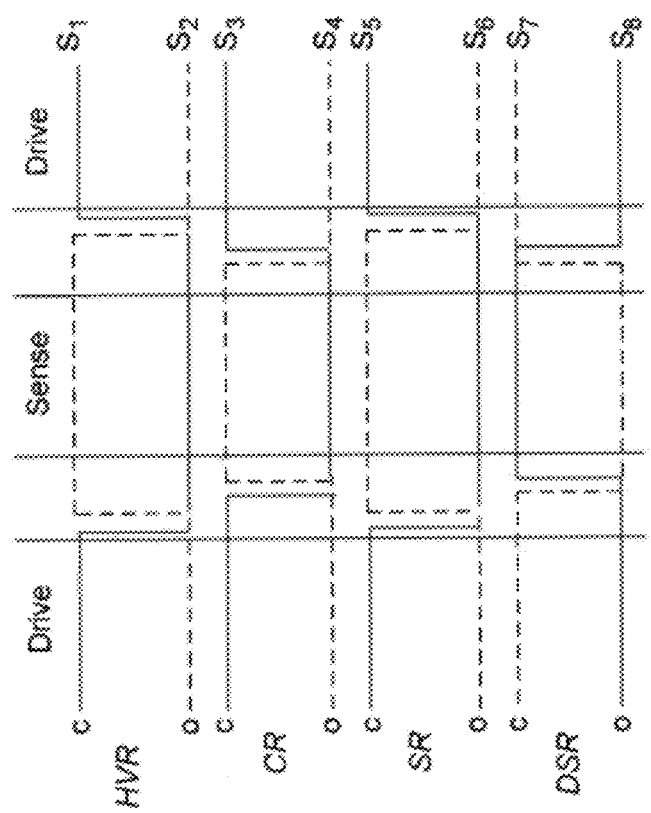
FIG. 21 is a timing diagram explaining operation of the circuit shown in FIG. 20.

FIG. 21 is a timing diagram explaining operation of the circuit shown in FIG. 20. Specifically, it explains operation of the relays in both drive and sense modes and as they transition between the modes. It is desirable to use single pole double through (SPDT) relays with good isolation properties. However, as an alternative, single pole single through (SPST) relays can be substituted. Of course, this increases the number of control signals needed.

Figure 22:
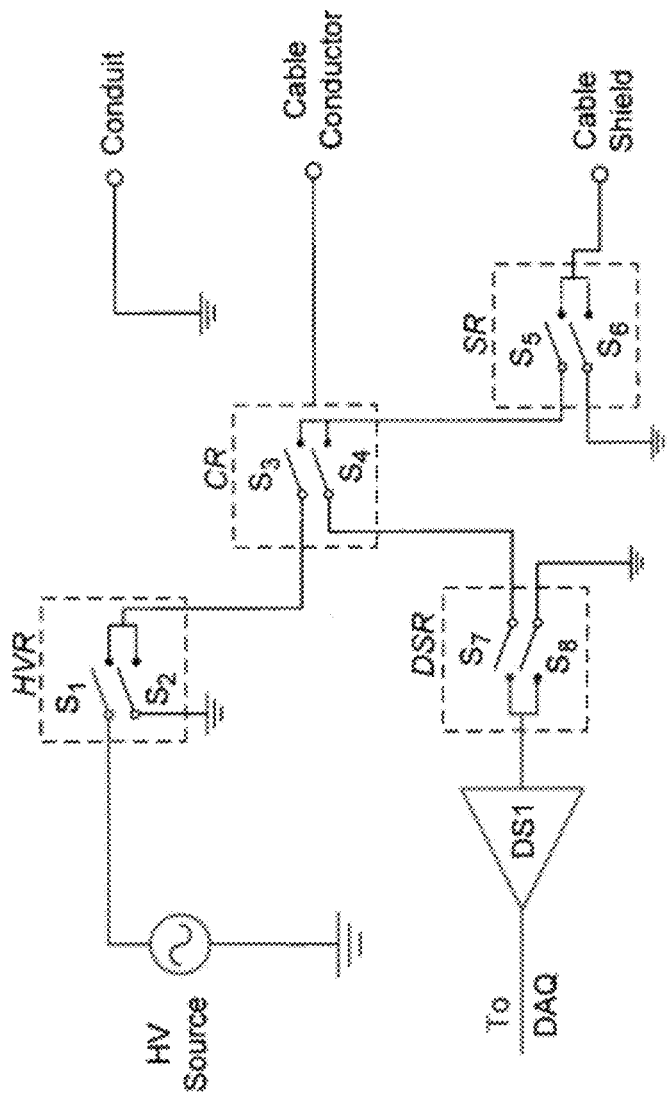
FIG. 22 is a schematic diagram of a switching network to multiplex cables implemented using SPST relays of a full tomography embodiment of the invention.

FIG. 22 is a schematic diagram of a switching network used to multiplex cables in an arrangement using SPDT relays.

Figure 23:
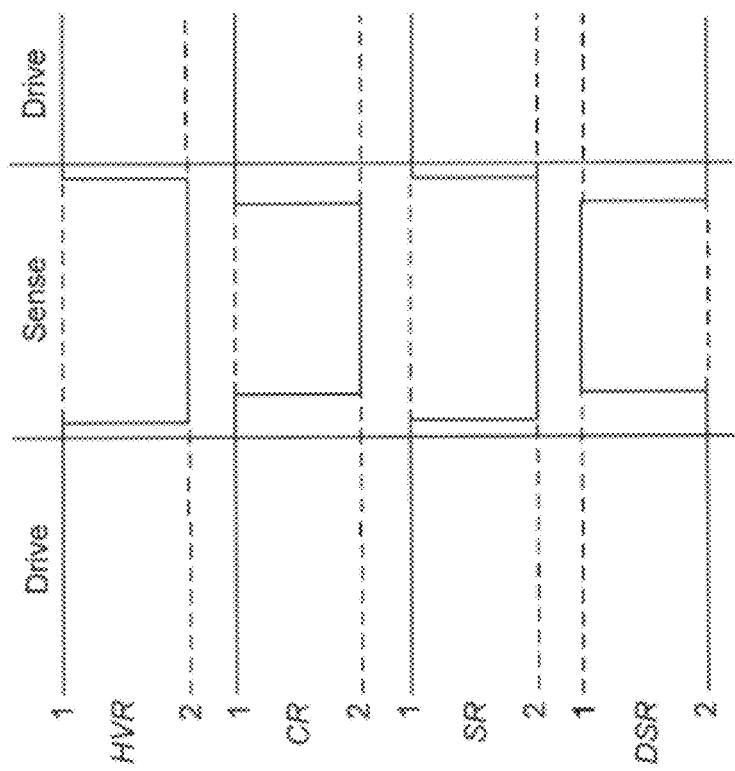
FIG. 23 is a timing diagram explaining operation of the circuit shown in FIG. 22.

FIG. 23 is a timing diagram explaining operation of the circuit shown in FIG. 22.

Figure 24:
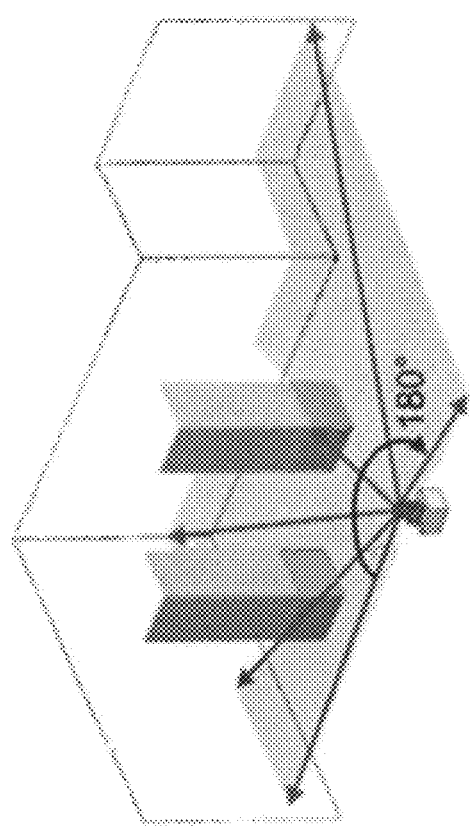
FIG. 24 schematically illustrates a laser line scanner that measures distance in a planar arc originating at the sensor according to a full tomography embodiment of the invention.

Since the position from a vehicle being inspected to sensor electrodes may vary, it is advantageous to utilize a distance measuring system so that positioning and measuring distances are accurately known. An embodiment of the invention utilizes a laser distance measurement system, as schematically generally illustrated in FIG. 24.

Figure 27:
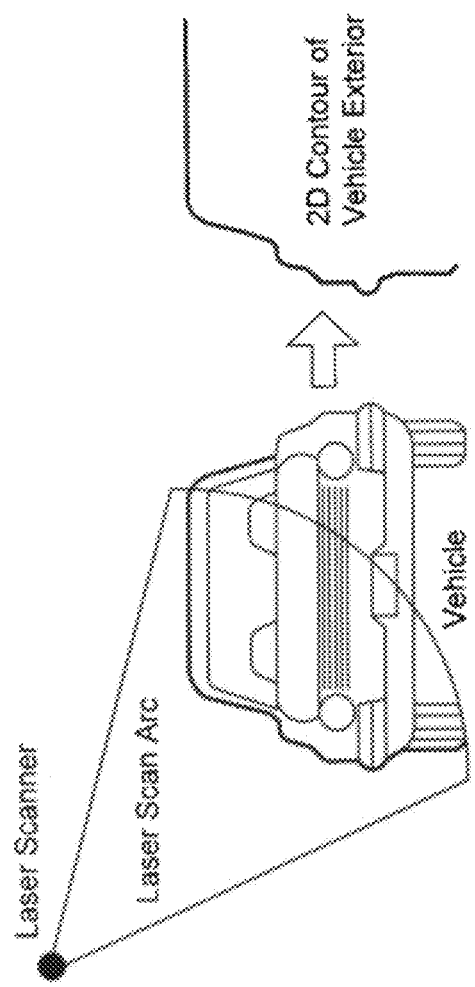
FIG. 27 shows a laser scanner measuring the exterior profile of a vehicle being inspected for potential target material according to a full tomography embodiment of the invention.

A practical laser ranging system for establishing the position of a vehicle with respect to electrodes is shown in FIG. 27. A laser line scanner 2702 measures distance from the sensor to surrounding objects in a planar arc 2704 originating at laser scanner 2702. This distance can be used to estimate the coupling capacitance between the proximate electrodes and the conducting object under test.

If the laser scanner is placed above and to the side of the vehicle with the measurement arc oriented vertically, it measures the exterior profile of the vehicle at one point along the vehicle's length, as shown in FIG. 27.

Figure 28:
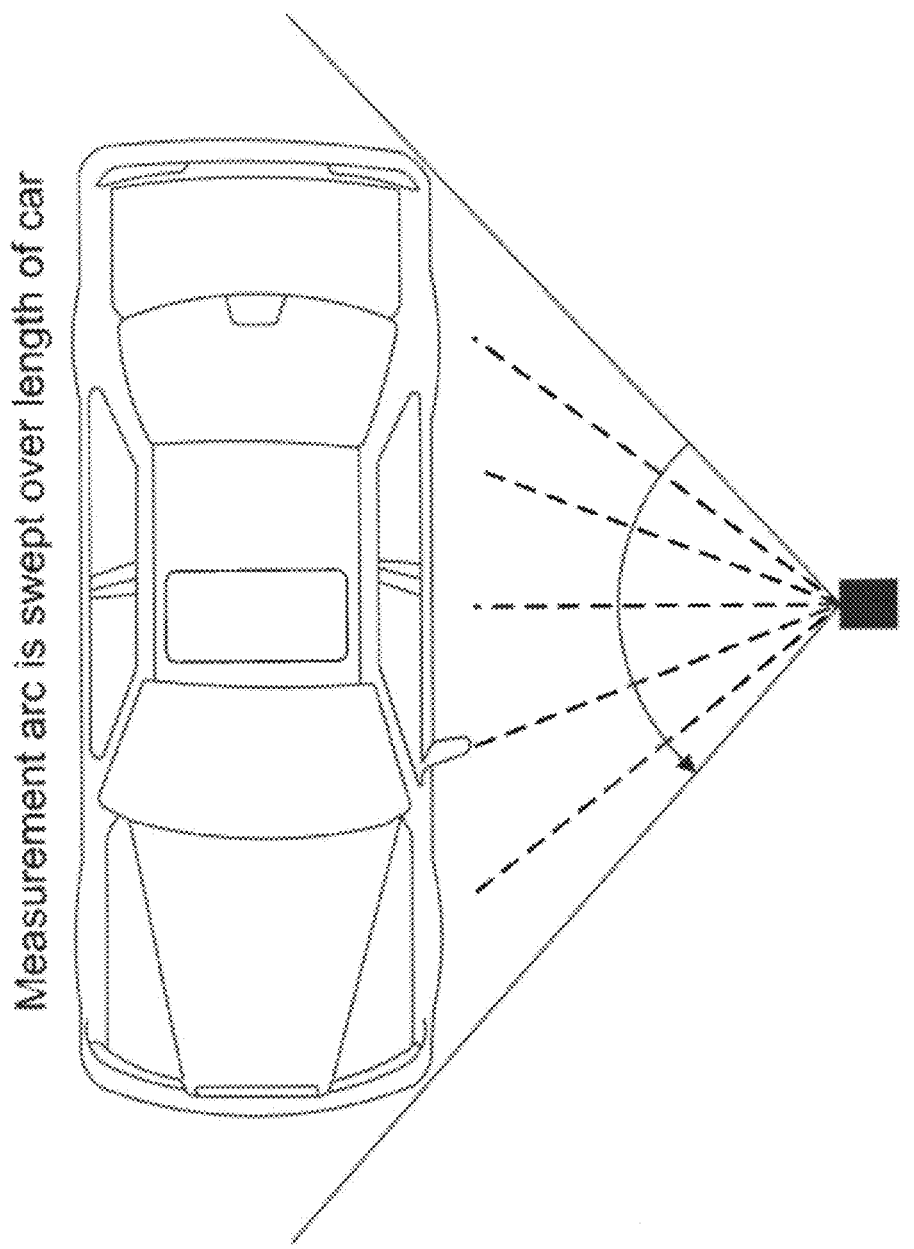
FIG. 28 is a schematic diagram showing that a rotary actuator can be used to rotate the laser scanner (FIG. 27) to sweep a measurement arc over the entire vehicle.

If a rotary actuator is used to rotate the laser scanner from side to side, the measurement arc can be swept over the entire length of the vehicle to produce a rough 3-dimensional (3D) profile of its exterior, as shown in FIG. 28, which shows a rotary actuator that rotates the laser scanner to sweep the measurement arc over the entire vehicle.

Figure 29:
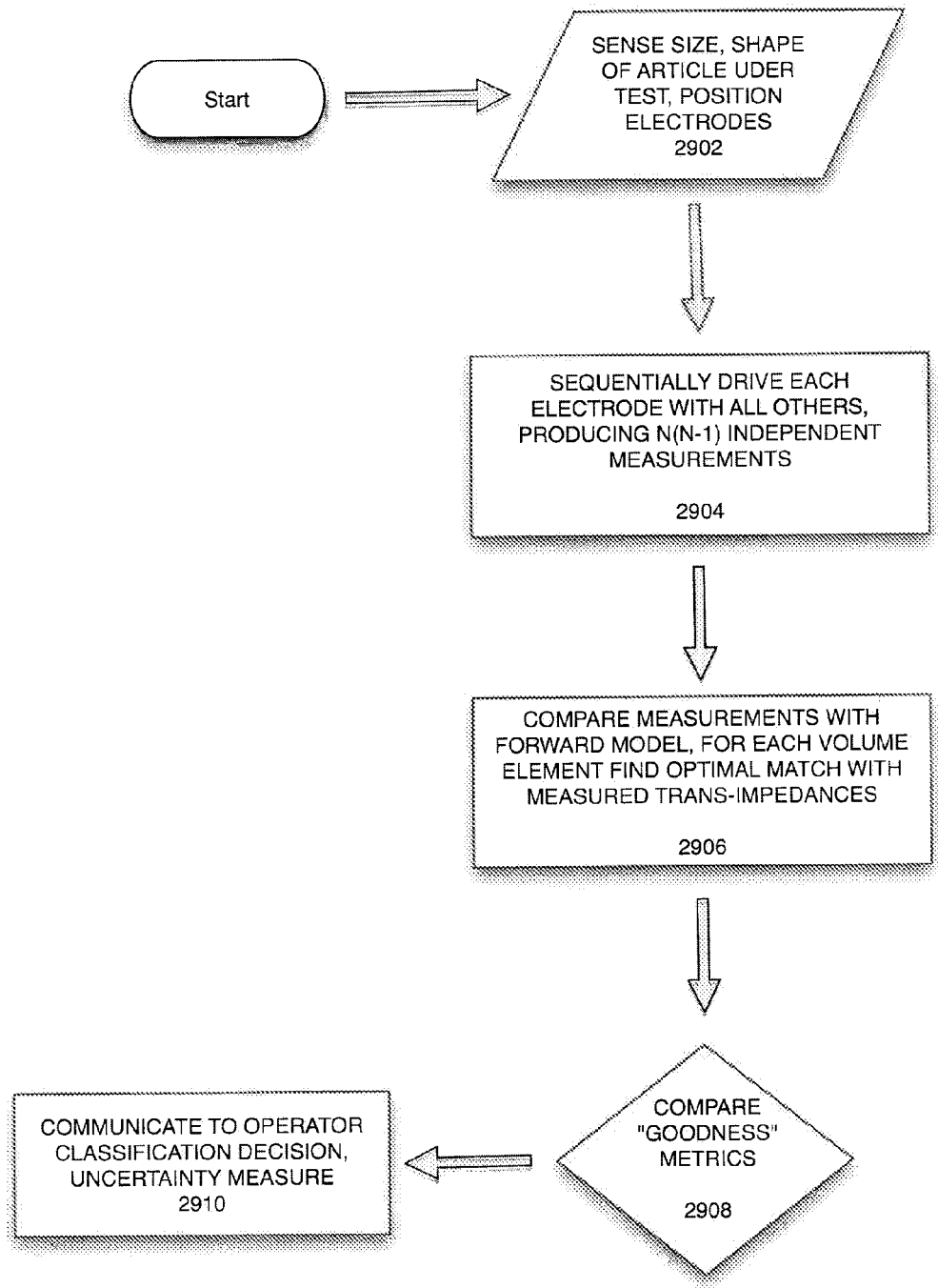
FIG. 29 is a flow chart of an exemplary tomographic process 2900 used to identify an unknown target material according to an embodiment of the invention.

According to an embodiment of the invention tomography and feature classification are combined to determine the presence of a material of interest within the object under test. FIG. 29 is a flow chart describing an exemplary tomographic process for identifying an unknown material according to an embodiment of the invention. The forward model referred to in FIG. 29 can be a forward model, such as shown in FIG. 26. The forward model includes a finite number (such as for example, 24 or 32) of internal compartments representing respective portions of a vehicle being examined. Within each compartment dielectric properties of a material are represented as a frequency dependent, parallel RC circuit. These equivalent circuit element values are processed by a classification algorithm that compares the recovered equivalent circuit values with those in a library of labeled dielectric signatures of materials of interest. The classifier classifies each compartment using the distance in feature space from the signature library. The actual classifier may be based on any of several methods well known to those of ordinary skill in the art.

FIG. 29 illustrates an exemplary tomographic process 2900 for identifying an unknown material. Process 2900 is carried out by an operator who can adaptively change various scanning parameters, such as which electrodes are driven, at what frequency and with what waveforms. Tomography process 2900 identifies whether or not a volume element of an environment being explored (for example, a vehicle) may contain a material of interest, and the degree of confidence with which that decision can be made. Process 2900 answers these questions by first computing what set of parameters (for a given vehicle, the location and material) results in the best match to the measurement data. Process 2900 subsequently computes a statistical metric to estimate the confidence that the parameters which best match the measured trans-impedances are unique and correct. For example, there can be a great deal of confidence in a solution that material "x" is present at location "α" if the feature vector derived from x, and α most closely match the feature vector derived from measurement data. The extent that the measurement data is not precisely matched by the best parameter can be interpreted as a measure of confidence that the parameters are correct.

Another measure of confidence taught in the present invention is the degradation of match quality for slight perturbations around the best match. For example, for the case of a vehicle under scan, the tomography process might conclude that for the make and model of vehicle presented, the best match is obtained with material "b" present at location "μ". Process 2900 would evaluate the match quality of other materials a and material c at location μ, as well as material b at nearby locations λ and location ν. Process 2900 would also evaluate the sensitivity of the solution of material b present at location μ over different vehicles and with confounding material present. Ideally, these perturbations would be well differentiated from the best solution of material b present at location μ. To the extent that the perturbations are not well differentiated, or only marginally differentiate from the solution, the confidence in the solution might be reduced.

Another measure of confidence is to start the inversion process with different starting assumptions. If the same computed solution is converged upon, confidence can be had in the solution.

At step 2902 the size and shape of an article under test is determined and electrodes are positioned. For example, where the object under scan is a vehicle, the make and model of the vehicle could be input by the user or determined from matching the size and shape of the vehicle with a library of contours of different vehicles that have been previously measured. Once the vehicle information is established, the electrodes can be automatically positioned to align with the windows. If the object under scan is a box or suitcase, the electrodes can be automatically positioned to accommodate the dimensions of the object.

At step 2904, the electrodes are sequentially driven. Measurements are made with each of the non-driven electrodes. This produces n(n−1) independent measurements for a group of n electrodes. At step 2906 the n(n−1) independent measurements are compared with the forward model (see FIG. 26).

In one embodiment scanning vehicles, the tomography process will produce equivalent parallel RC circuit element values for the forward model elements that represent, the material within predefined regions in the vehicle interior (compartments), the electrode-to-electrode coupling impedances, and the electrode-to-compartment coupling impedances. These equivalent circuit parameters have unique individual values and correlations among pairs of parameters that depend upon any of several vehicles or vehicle classes, and locations within those vehicles of contraband material. By collecting a training data base over the class of vehicles and contraband materials of interest measurements made during operation of the system are processing via the forward model based inversion process to a set of equivalent circuit parameters and compared to the values in the training set via a hypothesis testing based classification process. The comparison can be done using any of several classification algorithms, including without limitation k nearest neighbors, k means (with or without clustering), manifold learning or other techniques. Multivariate Gaussian models derived from training data sets large enough to estimate both expected value of the inversion process based feature vectors and the full covariance matrix representing the correlation properties between each pair of features have exhibited the ability to correctly identify contraband materials of interest over a wide range of conditions. Also taken into account are baseline vehicle identification data including without limitation previously measured responses of an empty vehicle of the same make and mode, temperature, vibrometry and other secondary data such as x rays for boxes, suitcases and containers used is cargo shipment.

Until this point the forward model is viewed as a two dimensional typology of an equivalent circuit model, however the present invention anticipates higher dimensioned equivalent circuit typologies. The planar equivalent circuit forward models described above can be extended/replaced with non-planar equivalent circuit forward models to explicitly represent the three dimensional distribution of materials within a object under test. These methods could be based on the use on electrode arrays positioned proximate to the object under test at both varying heights and positions.

In an alternative embodiment, a set of complex trans-impedance measurements taken at all of the electrodes is compared, using any of several classifiers, to an extensive training set derived from measurements, the forward model or both. In one embodiment the training set consists consisting of all contraband and confounding materials in a large number of locations in a large number of vehicles. This library of trans-impedance signature data will be used to develop a classifier. A variant of this embodiment assumes a training set consist of a finite number (N) of vehicles and places a finite number of materials (M) where the (K) materials of interest are included, in a finite number of locations (L). Each combination of a vehicle, material and location would define one of the possible N*M*L classes. In operation measured trans-impedance data are processed to yield a feature vector that would be compared with the N*M*L feature vectors produced during the training process. The classifier would assign a measurement to one of these N*M*L classes with a positive declaration of a material of interest being present if the data is classified in into any of the N*K*L classes corresponding to a material of interest.

As in the case of reduced order tomography, the permittivity signatures produced by an array on N sensors positioned circumferentially around the object under test is subject to pre-processing. This pre-processing step includes estimating parasitic ground, shielding and coupling capacitances based on a variety of factors, including precisely measured distances between the exterior surface and the several electrodes, and the response of the vehicle to low frequency excitation. Additionally, the measurement data can be preprocessed so that certain outlier measurements are discarded from a particular data set. In practice, there are numerous reasons for a dielectrometry measurement signal to be occasionally noisy. For example, noise may result from an occasional static discharge or a switching event in a nearby electronic circuit. The dielectric signatures are known to be smooth, and therefore signal variation outside of the smooth signature range can be considered noise and discarded before data is processed further.

At step 2908 "goodness" metrics are computed that indicate the reliability (confidence) of the computed solution. At step 2910 a computed decision specifying classification and certainty of classification is communicated to the operator.

Previous efforts to identify materials utilizing dielectrometry have utilized standalone sensors measuring complex dielectric permittivity of an unknown material of interest. According to the invention, it has been determined that it is possible to gain an identification advantage by using ancillary sensors to position the unknown material under test within the sensor array. Ancillary transducers can be used to induce a particular response in the material of interest to aid classification. Acoustic resonance of the object under test, mass distribution and other incidental measurements could be synergistically processed with the permittivity data developed by the invention in such a manner to improve the overall detection and classification of contraband substances. Dielectrometry for detection of contraband substances has an important attribute in that the factors that degrade the permittivity measurement are generally not the factors that degrade more conventional contraband detection sensing modalities (such as trace detection, systems that employ ionizing radiation and the like). In that sense the permittivity data developed by the invention is "orthogonal" to other sensing modalities. This orthogonal sensitivity means that permittivity data developed by any embodiment of the invention could be combined with other primary sensors, including trace detectors, systems that employ ionizing radiation and any other sensing modality to enhance the overall performance of that system.

Example Computer System

Figure 25:
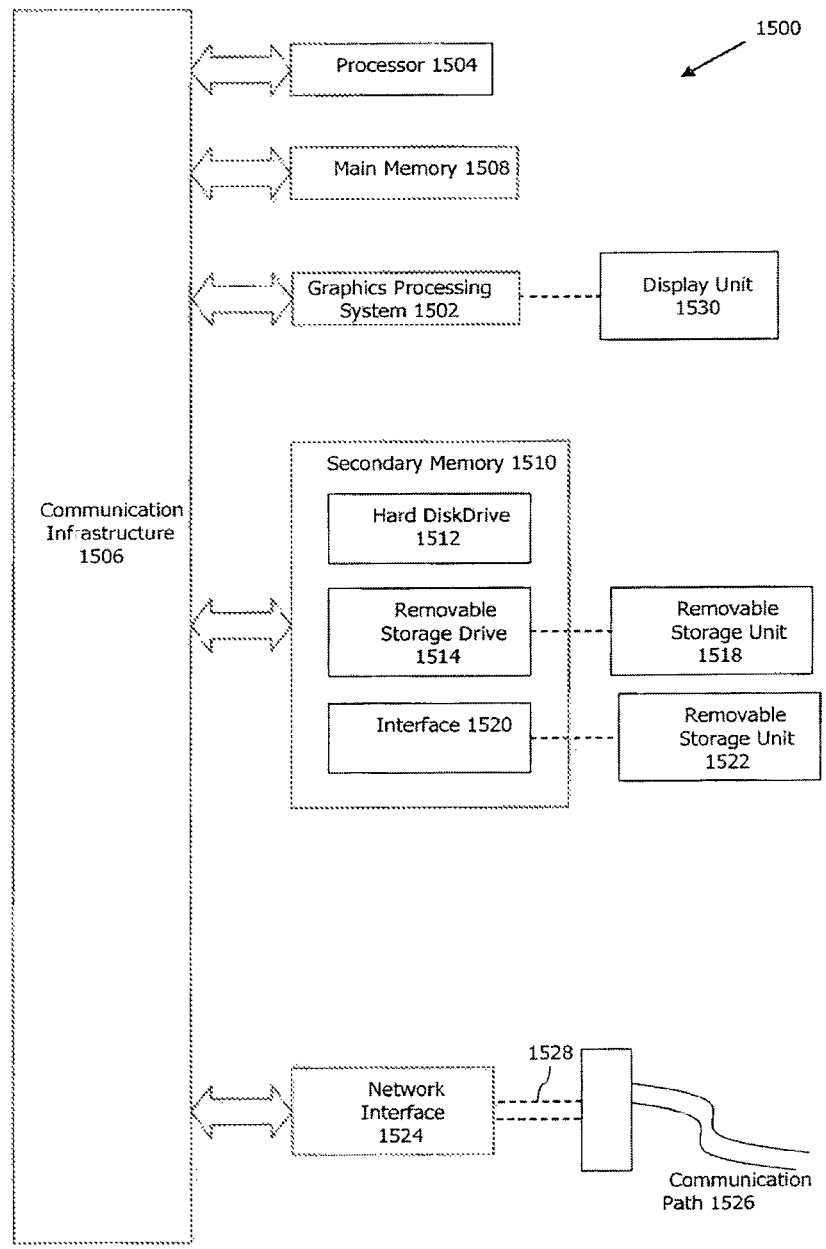
FIG. 25 is a block diagram of a computer system suitable for use in various embodiments of the invention.

Various aspects of the invention, such as the computing modules described herein, can be implemented by software, firmware, hardware, or a combination thereof. FIG. 25 illustrates an example computer system 2500 in which an embodiment of the invention, or portions thereof, can be implemented as computer-readable code. Various embodiments of the invention are described in terms of this example computer system 2500. After reading this description, it will become apparent to a person skilled in the relevant art how to implement the invention using other computer systems and/or computer architectures.

Computer system 2500 includes one or more processors, such as processor 2504. Processor 2504 can be a special purpose or a general purpose processor. Processor 2504 is connected to a communication infrastructure 2506 (for example, a bus or network). Computer system 2500 may also include a graphics processing system 2502 for rendering images to an associated display 2530.

Computer system 2500 also includes a main memory 2508, preferably random access memory (RAM), and may also include a secondary memory 2510. Secondary memory 2510 may include, for example, a hard disk drive 2512 and/or a removable storage drive 2514. Removable storage drive 2514 may comprise a floppy disk drive, a magnetic tape drive, an optical disk drive, a flash memory, or the like. The removable storage drive 2514 reads from and/or writes to a removable storage unit 2518 in a well known manner. Removable storage unit 2518 may comprise a floppy disk, magnetic tape, optical disk, etc. which is read by and written to by removable storage drive 2514. As will be appreciated by persons skilled in the relevant art(s), removable storage unit 2518 includes a computer usable storage medium having stored therein computer software and/or data.

In alternative implementations, secondary memory 2510 may include other similar means for allowing computer programs or other instructions to be loaded into computer system 2500. Such means may include, for example, a removable storage unit 2522 and an interface 2520. Examples of such means may include a program cartridge and cartridge interface (such as that found in video game devices), a removable memory chip (such as an EPROM, or PROM) and associated socket, and other removable storage units 2522 and interfaces 2520 which allow software and data to be transferred from the removable storage unit 2522 to computer system 2500.

Computer system 2500 may also include a communications interface 2524. Communications interface 2524 allows software and data to be transferred between computer system 2500 and external devices. Communications interface 2524 may include a modem, a network interface (such as an Ethernet card), a communications port, a PCMCIA slot and card, or the like. Software and data transferred via communications interface 2524 are in the form of signals 2528 which may be electronic, electromagnetic, optical, or other signals capable of being received by communications interface 2524. These signals 2528 are provided to communications interface 2524 via a communications path 2526. Communications path 2526 carries signals 2528 and may be implemented using wire or cable, fiber optics, a phone line, a cellular phone link, an RF link or other communications channels.

Computer programs (also called computer control logic) are stored in main memory 2508 and/or secondary memory 2510. Computer programs may also be received via communications interface 2524. Such computer programs, when executed, enable computer system 2500 to implement embodiments of the invention as discussed herein, such as the computing modules. In particular, the computer programs, when executed, enable processor 2504 to implement the methods of embodiments of the invention, including the methods implemented by the computing modules. Accordingly, such computer programs represent controllers of the computer system 1500. Where the invention is implemented using software, the software may be stored in a computer program product and loaded into computer system 2500 using removable storage drive 2514, interface 2520, hard drive 2512 or communications interface 2524.

Applications of the invention to various industrial fields, the invention and it embodiments are applicable to a wide range of measurement applications, including but not limited to detection of: (i) contraband in a stationary or moving vehicle, (ii) contraband cached in culverts or buried in the soil, particularly in non-metallic packaging (iii) contraband in shipping containers, suitcases and parcels, (iv) contraband in walls and otherwise cached in building structures, or other non-structural items, (v) contraband on humans or animals walking past a sensor or passing a portal, (vi) positioning the sensor physically forward of the operator and data linking sensor results to the operator (proximate sensing, remote read out), (vi) law enforcement applications including but not limited to scanning suspicious packages for contraband, gem stones, currency, (vi) smart houses, (vii) smart appliances (e.g., is there milk/how much milk is in the container, other point level sensing applications) and (viii) industrial/agricultural (i.e., how much grain is in the silo, or what grain is in the silo or is it still in good condition (e.g., by evaluating and monitoring moisture content) or (ix) quantitative control in any manufacturing process, such as the presence or quantity of impurities in a known substance, presence or quantity of reactants in a chemical process or (x) impurities in commercial commodities like fuel, packaged foods, etc., (xi) measurement of properties of stratified materials, such as multi-layered coatings and diffusion processes, (xii) detections of viruses, bacteria, and antibodies attached to the sensor surface, (xiii) detection of proximity of surfaces, for example in robotic applications, (xiv) determination of aging status of materials, (xv) detection of the presence of cracks and delaminations.

CONCLUSION

It is to be appreciated that the Detailed Description section, and not the Summary and Abstract sections, is intended to be used to interpret the claims. The Summary and Abstract sections can set forth one or more but not all exemplary embodiments of the invention as contemplated by the inventor(s), and thus, are not intended to limit the invention and the appended claims in any way.

The invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Various embodiments of the invention have been described above. It should be understood that they have been presented by way of example only, and not limitation. It will be apparent to persons skilled in the relevant art that various changes in form and detail can be made from those specifically described without departing from the spirit and scope of the invention. Thus, the breadth and scope of the invention should not be limited by any of the above-described exemplary embodiments, but should be defined only in accordance with the following claims and their equivalents.

What is claimed is:

1. A method for determining the presence, quantity, spatial distribution, and composition of a target material that may be present in an environment, the method comprising:
generating, using a pair of electrodes, a first electromagnetic field having a first set of characteristics, the first electromagnetic field interacting with the target material if present;
measuring a first trans-impedance between the pair of electrodes based on the generated first electromagnetic field;
generating, using the pair of electrodes, a second electromagnetic field having a second set of characteristics, the second electromagnetic field differing from the first electromagnetic field and the second electromagnetic field interacting with the target material if present;
measuring a second trans-impedance between the pair of electrodes based on the generated second electromagnetic field;
perturbing a forward model to compare the first trans-impedance to a first known intrinsic dielectric property of the target material and to compare the second trans-impedance to a second known intrinsic dielectric property of the target material, wherein the first known intrinsic dielectric property of the target material and the second known intrinsic dielectric property of the target material are stored in a library of known intrinsic dielectric properties of a plurality of materials, and the forward model is based on a lumped electrical circuit representation of the environment; and
determining the presence, quantity, and location of the target material within the environment based on the perturbing.

2. The method according to claim 1, wherein the target material is one or more of explosives, explosive precursors, narcotics, narcotics precursors, chemical and biological agents and their precursors and any other contraband.

3. The method according to claim 1, wherein the forward model is constructed and arranged so as to represent a two dimensional structure.

4. The method according to claim 1, wherein the forward model is constructed and arranged so as to represent a three dimensional structure.

5. The method according to claim 1, wherein at least one of the first and second electromagnetic fields is an AC field.

6. The method according to claim 1, wherein the second electromagnetic field differs from the first electromagnetic field in frequency.

7. The method according to claim 1, wherein the second electromagnetic field differs from the first electromagnetic field in a characteristic according to a predetermined program.

8. The method according to claim 1, wherein the pair of electrodes is part of an electrode array and electrodes of the array are constructed and arranged to be bimodal in that any electrode can operate in a drive mode and in a sense mode of operation.

9. The method according to claim 8, wherein a temporal and spatial sequence of drive and sense modes of operation occur according to a predetermined protocol or are adaptively modulated to resolve classification and spatial ambiguities.

10. The method according to claim 1, wherein the second electromagnetic field differs from the first electromagnetic field in field orientation with respect to the target material.

11. The method according to claim 1, further comprising controlling a characteristic of the second field interactively based on direct comparison of the measured first trans-impedance or based on residuals obtained from processing of the measured first trans-impedance with the forward model, intrinsic dielectric permittivity data stored in the library of known intrinsic dielectric properties, or both.

12. The method according to claim 1, wherein a goodness or uniqueness of a candidate target material's intrinsic properties is determined by a distance and gradient between a best solution and a next best solution.

13. The method according to claim 1, wherein the second electromagnetic field differs from the first electromagnetic field in voltage.

14. The method according to claim 1, wherein the second electromagnetic field differs from the first electromagnetic field in waveform.

15. The method according to claim 1, further comprising physically or otherwise moving the pair of electrodes interactively to resolve ambiguities in recovered estimates of dielectric properties of the target material being scanned.

16. The method of claim 15, wherein a subsequent scan is initialized with different characteristics of an excitation electromagnetic field, including without limitation its individual frequencies, frequency band, voltage, waveform, electrode orientation and excitation pattern based on goodness metrics from a previous scan.

17. The method according to claim 16, wherein the perturbing comprises utilizing a tomographic process.

18. The method according to claim 1, wherein the perturbing comprises utilizing wavelet analysis to extract information of a dielectric response of the material to excitation.

19. The method according to claim 1, wherein the determining comprises forming a complex dielectric permittivity data matrix consisting of trans-impedances, capacitance, dielectric constant, conductivity, and other related parameters and then analyzing that data matrix to extract information of a dielectric response of the material to excitation for any arbitrary combination of electrodes.

20. The method according to claim 1, further comprising:
utilizing a position sensor to locate a position of an object being scanned for the target material with respect to the generating, the measuring the first trans-impedance, the measuring the second trans-impedance, and processing that position information to enhance the analysis of the object being scanned for the target material.

21. The method according to claim 20, further comprising:
utilizing an optical sensor to identify the object under scan, wherein the identification of the object under scan is used to enhance the estimation of the material composition interior to the material under scan.

22. The method according to claim 1, further comprising:
inducing, using an ancillary transducer, a particular response in the target material to aid in its differentiation from environmental materials and identification by altering its complex dielectric permittivity in a predictable fashion.

23. The method according to claim 22, wherein the inducing comprises inducing changes in dielectric properties incidental to an applied magnetic field, acoustic, tone including sub aural tones, temperature change, density change or any other physical property of the target material.

24. The method according to claim 1, wherein the pair of electrodes comprise N pairs of side by side electrodes that are employed to generate the first and second electromagnetic fields, an active electrode is switched to cause an effective change in distance of target and environmental materials with respect to the pair of electrodes, the resulting change in dielectric permittivity being useful for resolving classification ambiguities, wherein N is an integer greater than 1.

25. The method according to claim 1, further comprising grounding a partially conducting object under test for the target material for the purpose of determining dielectric permittivity measurements of objects internal to the partially conducting object under test.

26. The method according to claim 25, wherein the grounding is carried out by means of a telescoping conducting whip or conductive brushes.

27. The method of claim 25, wherein iso-permittivity contours are developed to illustrate the spatial distribution of the determined dielectric permittivity measurements of the objects internal to the partially conducting object under test, with or without identification of each material of the objects internal to the partially conducting object under test.

28. The method of claim 27, wherein algorithms based upon manifold learning are used to reduce the dimensionality over which the determining must take place.

29. The method of claim 27, wherein a clustering or a classification algorithm is used to associate the measured first trans-impedance and the measured second trans-impedance and forward model with known complex dielectric permittivity characteristics.

30. The method of claim 27, using the forward model to normalize the measured first trans-impedance and the measured second trans-impedance for factors such as quantity, location within the partially conducting object under test, the grounding of the partially conducting object under test and proximity to other materials, such normalized first trans-impedance and second trans-impedance forming or augmenting a hypothesis training set.

31. The method of claim 27, wherein any of several distance metrics are employed to identify which combination of materials, packaging, quantity, and location most closely matches the measured first trans-impedance and the measured second trans-impedance.

32. The method according to claim 27, further comprising:
    adaptively selecting an integration time of the measured first trans-impedance based on a predetermined threshold of signal-to-noise ratio.

33. The method according to claim 32, wherein the adaptively selecting an integration time includes further turning off switching of intermediate amplification stages after an initial determination of input signal amplitude.

34. The method according to claim 1, wherein the measured first trans-impedance and the measured second trans-impedance are carried out using drive and sense electrodes and the method further comprises:
    measuring a distance from the electrodes to an object containing the target material using a non-impedance technique in order to compute the coupling capacitance between the sense and drive electrodes.

35. The method according to claim 34, wherein the measuring the distance from the electrodes to the object containing the target material is carried out using a laser beam.

36. The method according to claim 34, wherein the measuring the distance from the electrodes to the object containing the target material is carried out using an ultrasound beam.

37. The method according to claim 1, further comprising:
    adaptively selecting an integration time of the measured first trans-impedance based on a predetermined threshold of signal-to-noise ratio.

38. The method according to claim 37, wherein the adaptively selecting an integration time includes further turning off the switching of intermediate amplification stages after an initial determination of input signal amplitude.

* * * * *